US007033617B2

(12) United States Patent
Shyur et al.

(10) Patent No.: US 7,033,617 B2
(45) Date of Patent: Apr. 25, 2006

(54) **USE OF *ANOECTOCHILUS FORMOSANUS* PLANT EXTRACTS AND THEIR DERIVED FRACTIONS AS HERBAL MEDICINES OR NUTRACEUTICAL SUPPLEMENTS FOR CHEMOPREVENTION OR TREATMENT OF HUMAN MALIGNANCIES**

(75) Inventors: Lie-Fen Shyur, Taipei (TW); Ning-Sun Yang, Taipei (TW); Pei-Ling Kang, Taipei (TW); Show-Jane Sun, Taipei (TW); Sheng-Yang Wang, Taipei (TW)

(73) Assignee: Academia Sinica, Tapei (TW)

( * ) Notice: Subject to any disclaimer, the term of this patent is extended or adjusted under 35 U.S.C. 154(b) by 0 days.

(21) Appl. No.: 10/194,345

(22) Filed: Jul. 12, 2002

(65) Prior Publication Data

US 2004/0009239 A1 Jan. 15, 2004

(51) Int. Cl.
*A61K 35/78* (2006.01)
(52) U.S. Cl. .................................. 424/725
(58) Field of Classification Search ............. 424/725
See application file for complete search history.

(56) References Cited

U.S. PATENT DOCUMENTS 5,837,257 A * 11/1998 Tsai et al.

FOREIGN PATENT DOCUMENTS

| JP | 05155738 | * | 6/1993 |
|---|---|---|---|
| JP | 06-293655 | | 10/1994 |
| JP | 06293655 | * | 10/1994 |
| JP | 11092492 | | 4/1999 |
| JP | 2002-114693 | | 4/2002 |

OTHER PUBLICATIONS

Lin et al., American Journal of Chinese Medicine, 2000, vol. 28, No. 1, 87-96.*
Lin et al., American Journal of Chinese Medicine, vol. 28, No. 1, pp. 87-96.*
Wang et al., "Profiling and Characterization of Antioxidant Activities in *Anoectochilus formosanus* Hayata", Journal of Agricultural and Food Chemisty, (2002) 50(7) 1859-1865.
Due, Xiao-Ming et al., "Butanoic Acid Glucoside Compositionof Whole Body and In Vitro Plantlets of *Anoectochilus formosanus*", Phytochemistry (1998) 49(7) 1925-1928.
Lin, Chun-Ching et al., Antioxidant and Hepatoprotective Effects of *Anoectochilus formosanus* and *Gynostemma pentaphyllum*, American Journal of Chinese Medicine, (2000) 28(1) 87-96.
S. L. McKenna et al., "Molecular Mechansims of Programmed Cell Death", Advances in Biochemical Engineering/Biotechnology, vol. 62.

N. Ahmad et al., "Green Tea Constituent Epigallocatechin-3-Gallate and Induction of Apoptosis and Cell Cycle Arrest in Human Carcinoma Cells", Journal of the National Cancer Institute, vol. 89, No. 24, Dec. 17, 1997, pp. 1881-1886.
A. A. Beg et al., "An Essential Role for NF-κB in Preventing TNF-α-Induced Cell Death", Science, vol. 274, Nov. 1, 1996, pp. 782-784.
M. M. Bradford, "A Rapid and Sensitive Method for the Quantitation of Microgram Quantities of Protein Utilizing the Principle of Protein-Dye Binding", Analytical Biochemistry 72, pp. 248-254 (1976).
W. Bursch et al., "Cell Death by Apoptosis and its Protective Role Against Disease", TiPS—Jun. 1992 (vol. 13), pp. 245-251.
G. Fang, et al., ""Loop" Domain is Necessary for Taxol-induced Mobility Shift . . . ", Cancer Research 58, pp. 3202-3208, Aug. 1, 1998.
U. K. Laemmli, Nature, vol. 277, Aug. 15, 1970, pp. 680-685.
Flora of Taiwan, Orchidaceae, pp. 874-877.
Zheng-gang Liu, et al., "Dissection of TNF Receptor 1 Effector Functions: JNK . . . ", Cell, vol. 87, 565-576, Nov. 1, 1996.
Jen-Kun Lin, et al., "Cancer Chemoprevention by Tea Polyphenols . . . ", Biochemical Pharmacology, vol. 58, pp. 911-915, 1999.
Xuesong Liu, et al., "Induction of Apoptotic Program . . . ", Cell, vol. 86, 147-157, Jul. 12, 1999.
A. Monks et al., "Feasibility of a High-Flux Anticancer Drug . . . ". Journal of the National Cancer Institute, vol. 83, No. 11, Jun. 5, 1991.
T. Mosmann, "Rapid Colorimetric Assay for Cellular Growth . . . ", Journal of Immunological Methods, 65 (1983) 55-63.
C. Naujokat et al., "Tumor Necrosis Factor-α and Interferon-γ Induce . . . ", Biochemical and Biophysical Research Communications, 264, 813-819 (1999).
M. C. Raff, "Social Controls on Cell Survival and Cell Death", Nature, vol. 356, Apr. 2 1992, pp. 397-400.
T. Seufferlein et al., "Sphingosylphosphorylcholine Activation of Mitogen . . . ", The Journal of Biological Chemistry, vol. 270, No. 41 Issue of Oct. 13 pp. 24334-24342.
P. Skehan et al., " New Colorimetric Cytotoxicity Assay for Anticancer-Drug Screening", Journal of the National Cancer Institute, vol. 82, No. 13, Jul. 4, 1990, pp. 1107-1112.
G. T. Williams, "Programmed Cell Death: Apoptosis and Oncogenesis", Cell, vol. 65, 1097-1098, Jun. 28, 1991.

(Continued)

*Primary Examiner*—Michael Meller
(74) *Attorney, Agent, or Firm*—Cohen, Pontani, Lieberman & Pavane

(57) ABSTRACT

The present invention provides medicinally active extracts and fractions, and a method for preparing the same by extracting and fractioning constituents from the tissue of plant components of the *Anoectochilus* family. These active extracts and fractions are useful for preventing or inhibiting tumor growth.

8 Claims, 14 Drawing Sheets

OTHER PUBLICATIONS

B. B. Wolf, et al., "Suicidal Tendencies: Apoptotic Cell Death by Caspase Family Porteinases", The Journal of Biological Chemistry, vol. 274, No. 29, Issue of Jul. 16, pp. 20049-20052, 1999.

S. Wright et al., "Inhibition of Apoptosis as a Mechanism of Tumor Promotion", Tumor Promoters Inhibit Apoptosis, pp. 654-660.

J. Yang et al., "Prevention of Apoptosis by Bcl-2: Release of Cytochrome c . . . ", Science, vol. 275, Feb. 21, 1997, 1129-1132.

G. Zhang et al., "Early Detection of Apoptosis Using a Fluorescent Conjugate of Annexin V", BioTechniques, vol. 23, No. 3 (1997), pp. 525-531 (Sep. 1997).

* cited by examiner

Fig. 3. Anti-cell proliferation effect of the total plant extract and bio-organically fractionated extracts of *A. formosanus* on MCF-7 human mammary carcinoma, HepG2 human hepatoma, and B16 mouse melanoma cells.

Fig. 4. Light microscopy analysis of cell morphology of MCF-7 cells without (A) or with the treatment of total crude extract (AF-Hot) (B), AH-sup fraction (C), and EA fraction (D) of *A. formosanus*.

Fig. 6. Flow cytometric analysis of vehicle-treated (control) and EA fraction-treated MCF-7 human mammary adenocarcinoma cells as a function of treatment time.

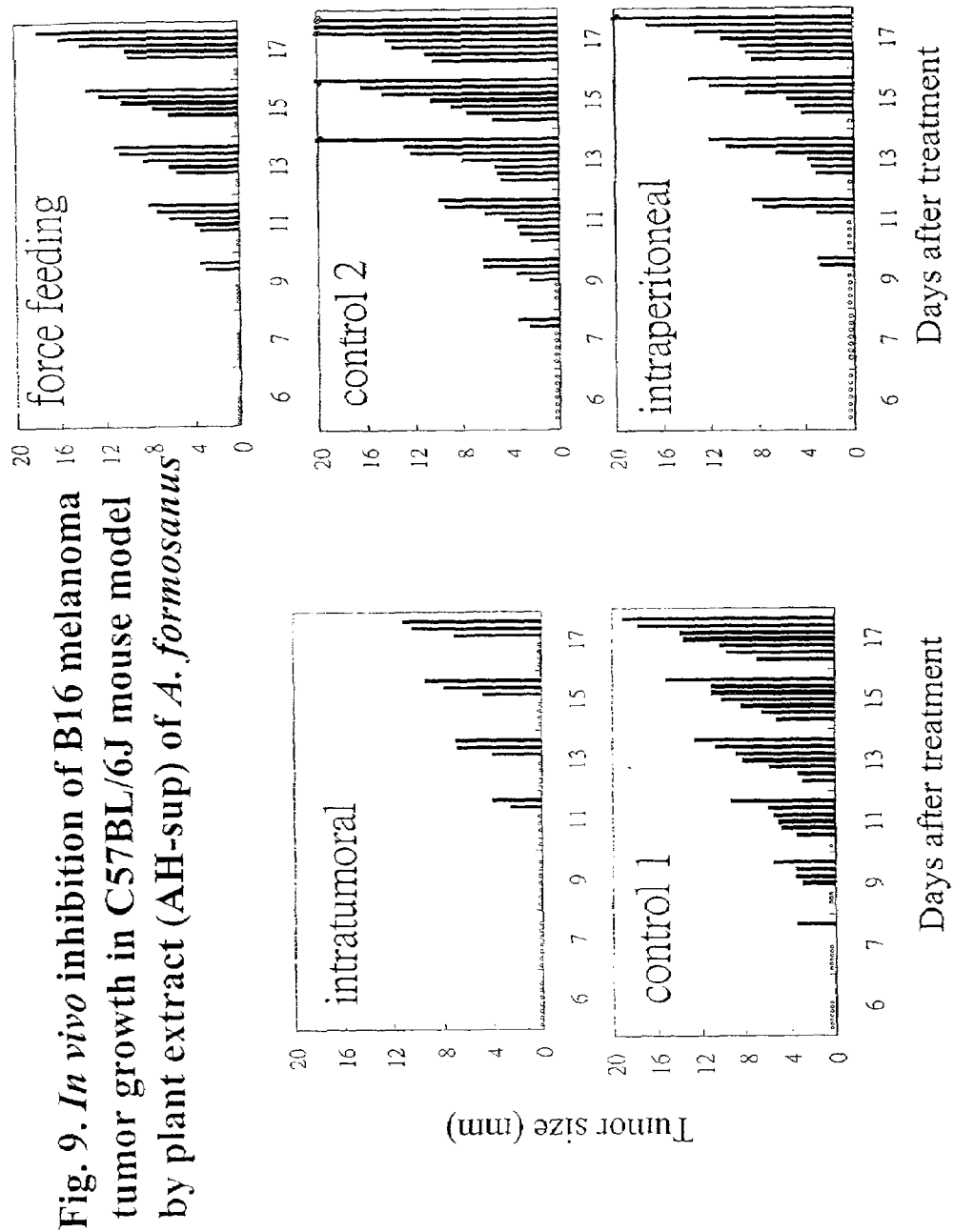
Fig. 9. *In vivo* inhibition of B16 melanoma tumor growth in C57BL/6J mouse model by plant extract (AH-sup) of *A. formosanus*

USE OF *ANOECTOCHILUS FORMOSANUS* PLANT EXTRACTS AND THEIR DERIVED FRACTIONS AS HERBAL MEDICINES OR NUTRACEUTICAL SUPPLEMENTS FOR CHEMOPREVENTION OR TREATMENT OF HUMAN MALIGNANCIES

BACKGROUND OF THE INVENTION

Field of the Invention

*Anoectochilus formosanus* Hayata (Orchidaceae) is an indigenous and important Taiwanese medicinal plant and has been used popularly as a nutraceutical herbal tea in Taiwan and other Asian countries. This herbal plant is also called "King Medicine" due to its diverse pharmacological effects such as liver-protection, cancer-prevention, diabetes, and for treatment of cardiovascular diseases (Kan, 1986). However, limited scientifically proven information is available on the bioactivity, physiological function, and specific clinical efficacy of this herbal orchid plant.

Apoptosis is a mechanistically driven form of cell death that is either developmentally regulated or activated in response to specific sets of stimuli or various forms of cell injury. It is now evident that many cancer cells can circumvent the normal apoptotic mechanisms to avoid their self-destruction. Many previous reports have suggested that the induction of apoptosis via the mediation with immune defense mechanism (Williams, 1991; Bursch et al., 1992) or other tissue-specific homeostatic controls (Raff, 1992) may contribute as an important process for elimination of nascent tumor cells. Recent advances in understanding the mode of action of anti-cancer agents indicate that regardless of the diverse nature of anti-cancer drugs, most of them can elicit apoptosis in targeted test tumor cells (Whllie et al., 1980; Jiang et al., 1996). Moreover, over-expression of certain "anti-apoptotic" proteins (e.g., Bcl-2 or Bclx$_L$) can inhibit apoptosis induced by anti-cancer agents including Taxol, ara-C, and etoposide (Fang et al., 1998). Conversely, numbers of known or suspected tumor promoters, e.g., phorbol myristate acetate (PMA), 1,1-bis(p-mezerein, diethylstilbestrol (DDT), saccharin, aflatoxin, etc., are known to induce resistance to apoptosis in a variety of tested cell types, indicating that the effect on inhibition of apoptosis is apparently mediated via a mechanism of tumor promotion (Wright et al., 1994). Therefore, it would be advantageous to tip the balance in favor of apoptosis over mitosis as cancer chemotherapy and preventative approaches.

There are recent indications that apoptosis involves the disruption of mitochondrial membrane integrity and results in the release of cytochrome c from mitochondria into cytosol, and that this sequence is decisive for the cell death process (Liu et al., 1996; Yang et al., 1997). Several anti-tumor drugs, e.g., Taxol and etoposide, with a diverse spectrum of target molecules, have been also shown to cause the release of mitochondrial components, and result in cytosolic accumulation of cytochrome c (Fang et al., 1998). The cellular mechanisms known to involve the process of apoptosis is the regulation of biochemical activities of a family of cysteine proteases designated as caspases.

In vitro tumor-inhibition screening systems with a bioactivity-based evaluation principal, using a panel of human tumor cell lines correlated to different types of cancerous diseases, and coupled with tetrazolium (MTT) assay and a protein-binding dye (sulforhodamine B) assay, have been developed by research groups at the National Cancer Institute (NCI), USA (Monks et al., 1991). These assays in essence are to measure tumor cell viability, growth, and cellular biochemistry behaviors. Following various pilot-screening studies, a screening rate of 400 compounds per week was achieved by Monks and coworkers and other groups at NCI, USA. Among the at least 8000 single compounds that have been screened to date, only a limited number of test samples (about 30) have shown significant, reproducible and stringent in vitro anti-tumor cell activity. Of that limited number, only approximately 8–10 compounds have shown an in vivo anti-tumor activity without excessive toxicity, and have been further tested in human clinical trials. This task and the results have illustrated the great difficulty of screening single compounds for cancer drug delivery.

A much faster, systematic strategy of using combinatorial chemistry and high throughput systems for drug screening is now commercially available, and is being actively employed by a number of pharmacological companies for new drug discoveries. It is also being appreciated as "not necessarily so straightforward" for cancer drug discoveries and consideration is being given to combined compounds or "cocktails." (Dr. G. Craggi, International Conference on Traditional Chinese Medicine Aug. 30-Sep. 2, 2000, Maryland, USA). This strategy of using crude or partially purified plant secondary metabolites/phytochemicals as a mixture of compounds for drug discovery, food supplements and nutraceuticals is the main policy and direction of the National Center of Complementary and Alternative Medicine (NCCAM) recently set up in the United States. Our research and this invention were designed with this new strategy and direction in mind. A most recent systematic effort of this approach employed for medicinal plants on tumor prevention and inhibition activities has also been studied on green tea and its derived active compound, epigallocatechin-3-gallate (EGCG)(Lin et al., 1999; Ahmad et al., 1997).

SUMMARY OF THE INVENTION

The present invention is in the herbal plant extracts of the Anoectochilus family of plants and in particular *Anoectochilus formosanus* ("*A. formosanus*"), prepared either as crude but defined plant extracts or as bioorganic-chemically fractionated plant metabolic compounds, a method for their preparation, compositions containing such extracts and in their use for chemo-prevention, or complementary/alternative control of various human malignant diseases.

Other species of *Anoectochilus*, for instance, *A. koshunensis* or cultivars from China, America, or Vietnam, have also been increasingly used as substitutes of *A. formosanus* for herbal medicines or nutraceuticals in Asian countries. Plant extracts of these Anoectochilus plants and their derivatives may also possess similar anti-tumor or tumor-prevention activities, and thus be potentially useful as specific pharmaceuticals or nutraceuticals.

This invention includes the use of such extracts and their phytochemical derivatives as tumor-prevention or tumor-inhibition remedies or nutraceuticals. Efficacious tumor cell-inhibition activities, that may be specifically potent against melanoma, breast cancer and hepatoma tumors, are defined here to confer prevention, control or suppression of growth of solid tumors, and this may potentially benefit normal individuals or cancer patients. Administration of herbal plant extracts to humans, either as non-symptomatic or as cancerous patients, may be by oral delivery (liquid-drinking), intra-tumoral (intra-dermal) injection, intra-peritoneal injection, topical application, or even intravenous injection of partially purified plant extracts.

Another aspect of the invention includes a process for obtaining the extracts of the invention either as a crude extract, a fraction derived from the crude extract or a subfraction. These extracts are obtained by one or more extraction steps using certain solvents and/or for specified extraction periods.

In other embodiments, the extracts or fractions are subjected to subsequent processing to obtain a more refined form.

In the invention, plant materials are grown under specific and constant green house conditions. The plant tissues are harvested under specified conditions, finely homogenized, and extracted with an aqueous medium, such as water, at, for example, 90–100° C., followed by a stepwise gradient fractionation. Further partitioned fractions lead to identification of useful index compounds which can be characterized by IR, mass, and NMR spectrometric analyses. The consistency and quality of lot-to-lot variations of the plant extracts can thus be monitored, adjusted, standardized or controlled by normalizing the levels of index compounds for ingredient/compound composition and profiling in specific plant extracts or the derived bio-organic solvent fractionation. After such normalization/standardization and quality control/analysis (QC/QA) measures, the obtained preparations of bioactive plant crude extracts or the derived organic fractions, can then be defined and systematized for use as nutraceuticals or remedies for prevention/control of tumor growth and related malignancies.

The use of the plant extracts and the derived fractions in in vitro (cell culture) cytotoxicity experiments, using MTT and $^3$H-thymidine incorporation assays, confers an effective inhibitory effect on cell-proliferation activities against MCF-7 cells (human breast adenocarcinoma), B16 cells (mouse melanoma), human hepatoma HepG2 of human or mouse tumor origin. The results obtained from in vitro cytotoxicity studies demonstrate that the kinetics of inhibition of tumor cell proliferation is a dose-dependent effect.

The invention also exhibits an inhibitory effect on in vivo tumor growth, using mouse B16 melanoma cells/C57 black mouse as the target tumor/animal model system. Intratumoral injections of *A. formosanus* extracts effectively inhibit B16 tumor growth in vivo, and a very significant effect on reduction of tumor growth was detected when *A. formosanus* extract is administered intra-peritoneally. A detectable effect is also observed in test mice by oral force-feeding.

Fluorescent microscopy and flow cytometry analyses show that the observed cell-killing effects of *A. formosanus* extract on the test tumor cells is apparently mediated through the process of programmed cell death (the so called "apoptosis"). We demonstrated in this invention that apoptosis of MCF-7 cells was medicated via the expression of Fas ligand (FasL) signaling pathway. Western-blot analyses of various signaling proteins involved in known apoptotic pathways showed that the expression levels of apical caspases (e.g., caspases 8 and 9), effecter caspases (e.g., caspase 7) cytochrome c, and poly-ADP ribose polymerase (PARP) protein molecules are significantly and specifically affected, when MCF-7 human mammary tumor cells are treated with *A. formosanus* plant extracts. A possible mechanism for the apoptosis in MCF-7 tumor cells as induced by the plant extract of *A. formosanus* is also proposed in this invention. A significant fluctuation of activity, increase and then decrease, of the caspase 3-like and caspase 8 activity is detected in good association with the killing of B16 melanoma cells, resulting as a function of time with the treatment of *A. formosanus* extract. These results strongly suggest that specific types of cell biological mechanism(s) or pathways, not general "intoxication of cells", are responsible for the observed anti-tumor cell effect of *A. formosanus*.

Other beneficial aspects of the invention include:
an essentially non-chemical technique or procedure, (i.e., no synthetic compounds, no buffer, and no toxic organic solvent) using boiling water for 0.1 to 500 minutes for aqueous and bio-organic extraction;
the use of a simple ethanol stepwise gradient (50 to 87.5%, v/v) extraction procedure to obtain a more biologically potent sub-fraction, i.e., the AH-sup fraction;
the further bio-organic extraction of AH-sup with ethyl acetate and butanol to yield groups of more purified or enriched metabolic compounds, which can confer a significant and higher level of anti-tumor activity than that from total crude extracts;
the preparation of a fraction (AH-sup), as derived from the total, crude aqueous extract (AF-Hot), which shows a high level of cytotoxicity on mouse B 16 melanoma, MCF-7 human mammary carcinoma and HepG2 human hepatoma cells in vitro, as compared to the activities obtained from other fractions (AF-Hot, AH-I, AH-II, and AH-III fractions);
the further bio-organic fractionation of the AH-sup fraction to yield three subfractions (designated as EA, BuOH, and Water fractions) which, based on the MTT assay shows the EA fraction, as compared to that of those obtained from AH-sup, BuOH, and Water fractions to have the most significant anti-tumor cell effect;

The plant extracts of the invention show the ability to inhibit tumor growth:
a) based on MTT assay and flow cytometry analysis, the AH-sup BuOH, and EA fractions of *A. formosanus* show different levels of anti-tumor cell proliferation effect, varying among the three tested cell lines, suggesting the *A. formosanus* plant extracts performed with differential anti-tumor or tumor-prevention activities;
b) in the case of HepG2 human hepatoma cells, a very significant cell-killing effect is observed when HepG2 cells are treated with the fractionated plant extracts, especially the EA fraction hence, the crude extract of *A. formosanus* may be used with minimal toxicity to liver cells, and can be more potent in treating other forms of tumor;
c) an anti-melanoma effect of the AH-sup or crude plant extracts when CS7BL/6J mice harboring B16 melanoma tumors are treated in situ intra-tumorally, intra-peritoneally, or orally fed with plant extracts of *A. formosanus* (AH-sup), i.e. the growth of B 16 tumor can be effectively inhibited in mice;

The animal model study in vivo showed that intra-tumoral, intra-peritoneal, and the oral-force feeding/drinking methods for delivery of *A. formosanus* plant extracts into animals can result in appreciable levels in inhibition of tumor growth, and hence be potentially useful for treatment or prevention of certain cancers.

The various features of novelty which characterize the invention are pointed out in particularity in the claims annexed to and forming a part of the disclosure. For a better understanding of the invention, its operating advantages, and specific objects attained by its use, reference should be made to the following drawings and description of the preferred embodiments of the invention.

Cell viability was measured 48 hours post-treatment of test cells with varying dosage of crude extract (AF-Hot) as indicated in the presence or absence of fetal bovine serum, using MTT assays. Each data point was obtained from the average of at least triplicate test samples.

Figure 3:
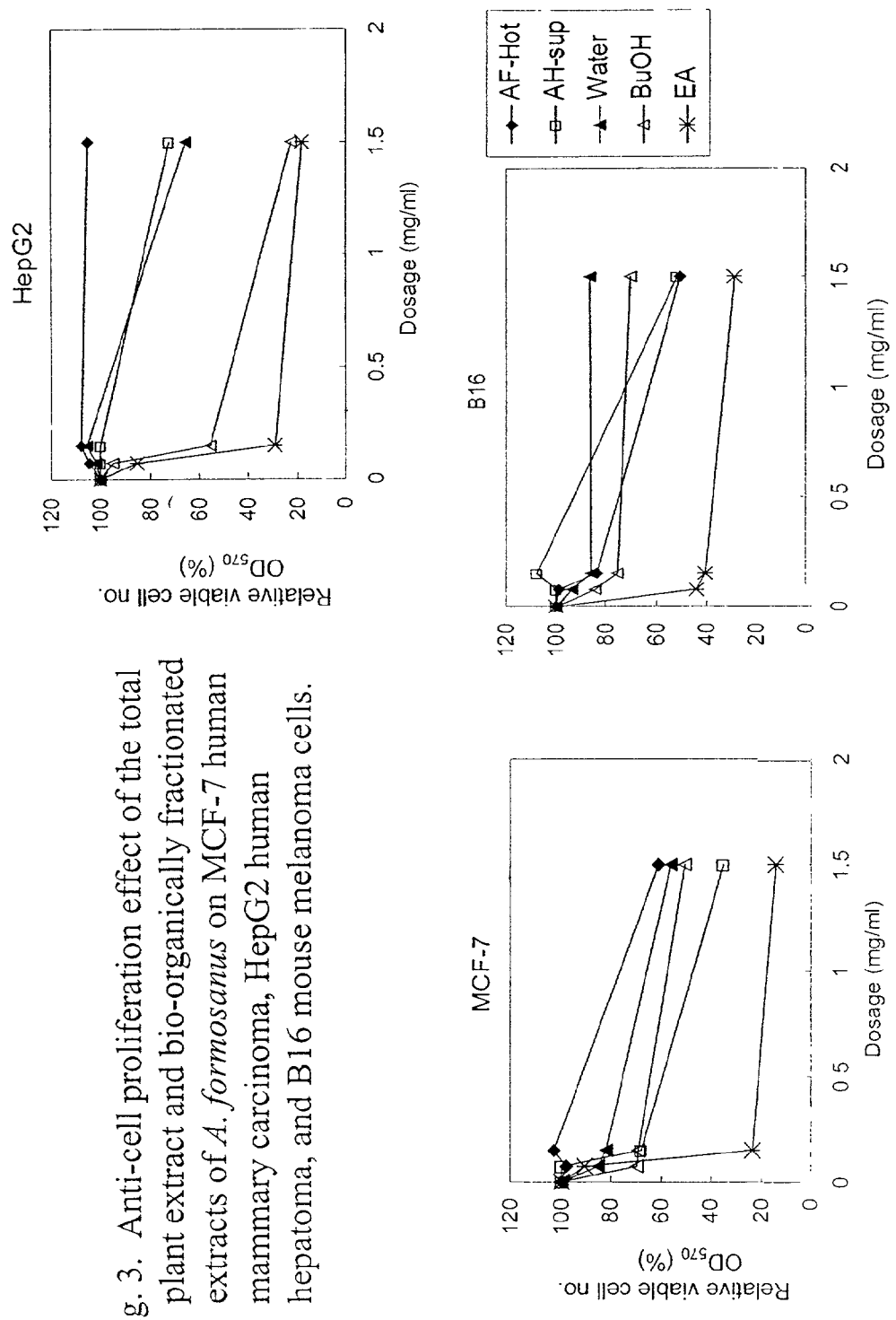

FIG. 3. Anti-cell proliferation effect of the total plant extract and bio-organically fractionated extracts of *A. formosanus* on MCF-7 mammary, HepG2 hepatoma, and B16 melanoma cell lines.

Cell viability was measured at 48 hours post-treatment of test cells with various dosages of crude extract (AF-Hot) and the derived fractions (AH-sup, EA, BuOH, and Water fractions, respectively), using MTT assays. Each data point was obtained from the average of at least triplicate samples.

Figure 4:
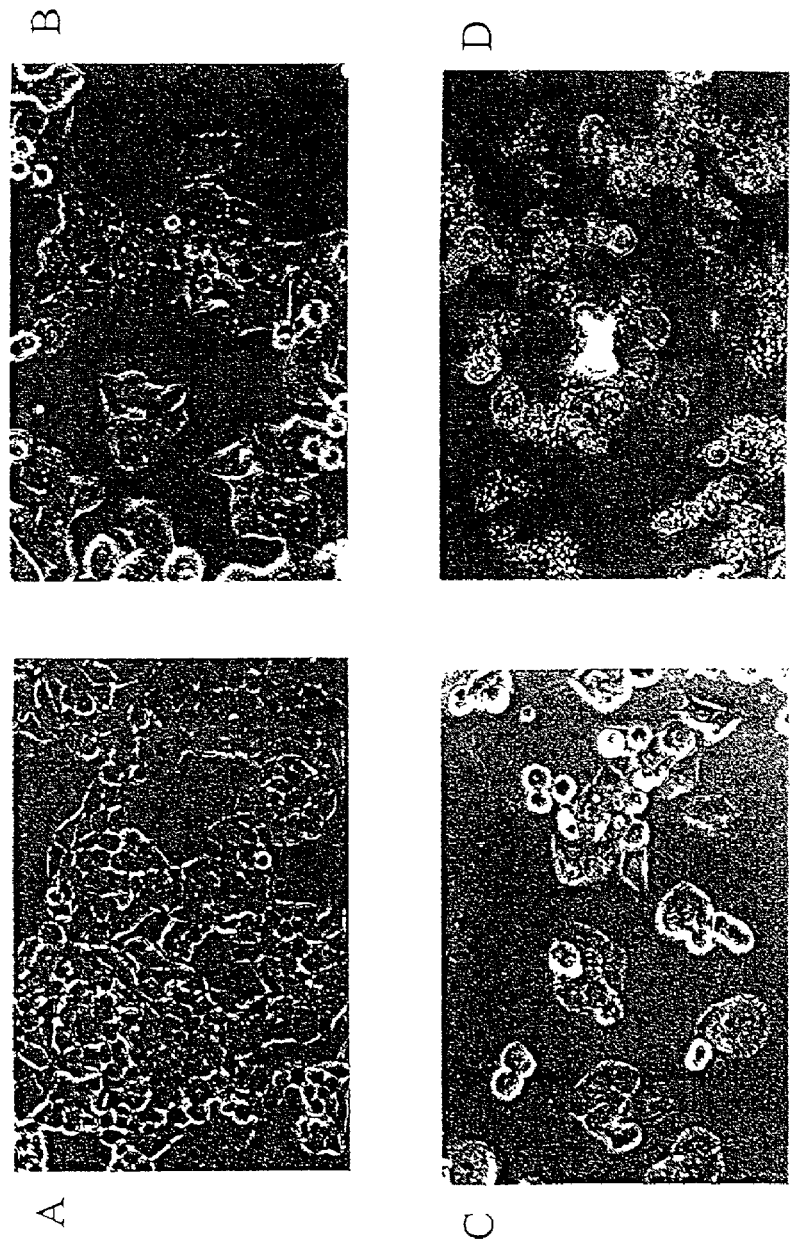

FIG. 4. Light microscopy analysis of cell morphology of MCF-7 cells without (A) and with the treatment of total crude extract (AF-Hot) (B), AH-sup fraction (C), and EA fraction (D) of *A. formosanus*.

MCF-7 cells were incubated in RPMI 1640 medium spiked either with phosphate buffered saline (A, control) or treated with 1 mg/ml of indicated plant extracts of *A. formosanus* for 48 hours. Each photomicrograph was taken with an Olympus PM-30 camera installed on an Olympus CK4O microscope with 200-fold magnification.

Figure 5:
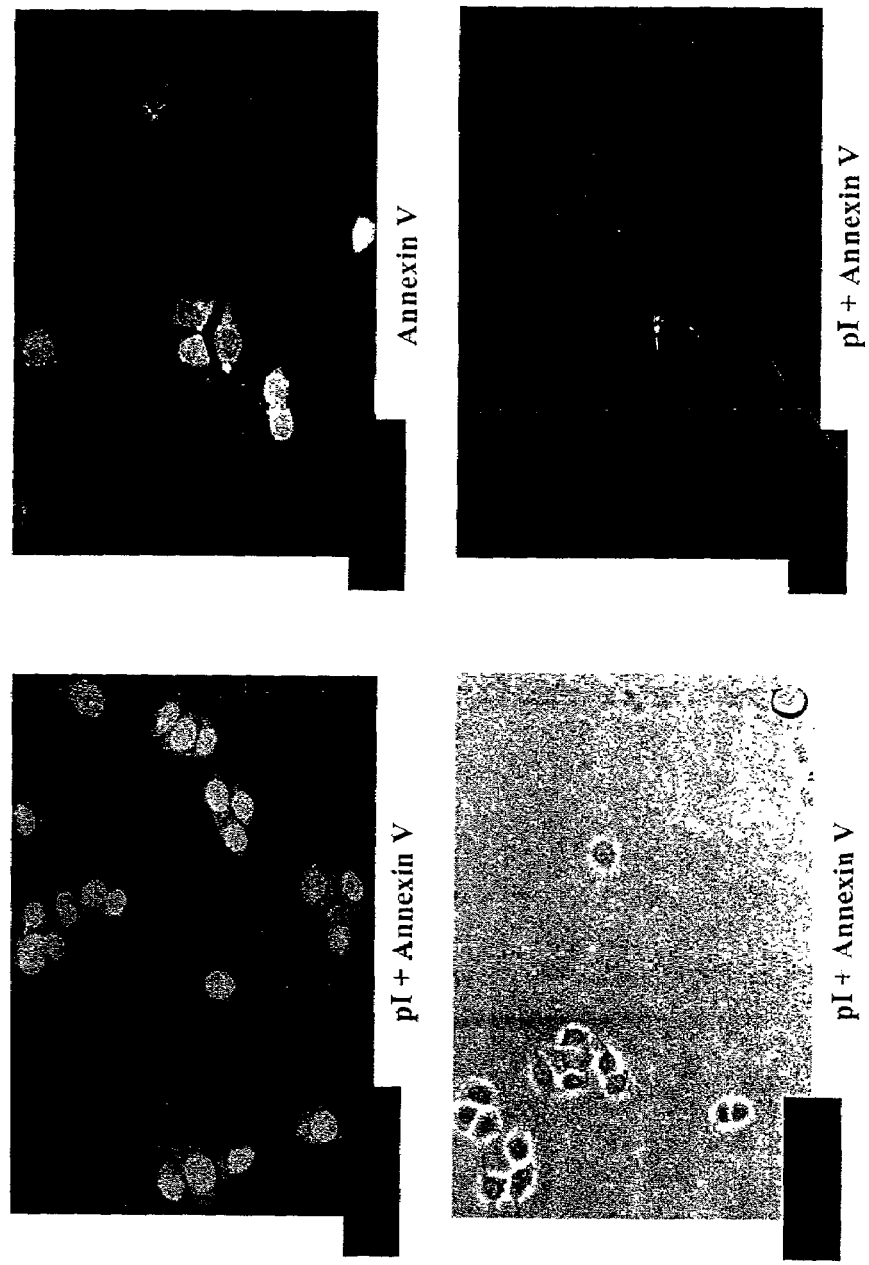

FIG. 5. Microscopic analysis of normal or apoptotic MCF-7 cells at the cellular level, as stained with Annexin-V and propidium iodide (PI).

MCF-7 cells were treated with EA fraction (1 mg/ml) for 4 hours and then stained with PI and Annexin-V (A) or with Annexin-V only (B). C & D were the control cells treated with vehicle (0.4% DMSO) and stained with PI and Annexin-V. A, B, and D were fluorescent photomicrography taken with an Olympus PM-30 camera installed on a Nikon ECLIPSE E800 microscope with 200-fold magnification using B-2A filter (Ex 450–490), and C was a brightfield view of D.

Figure 6:
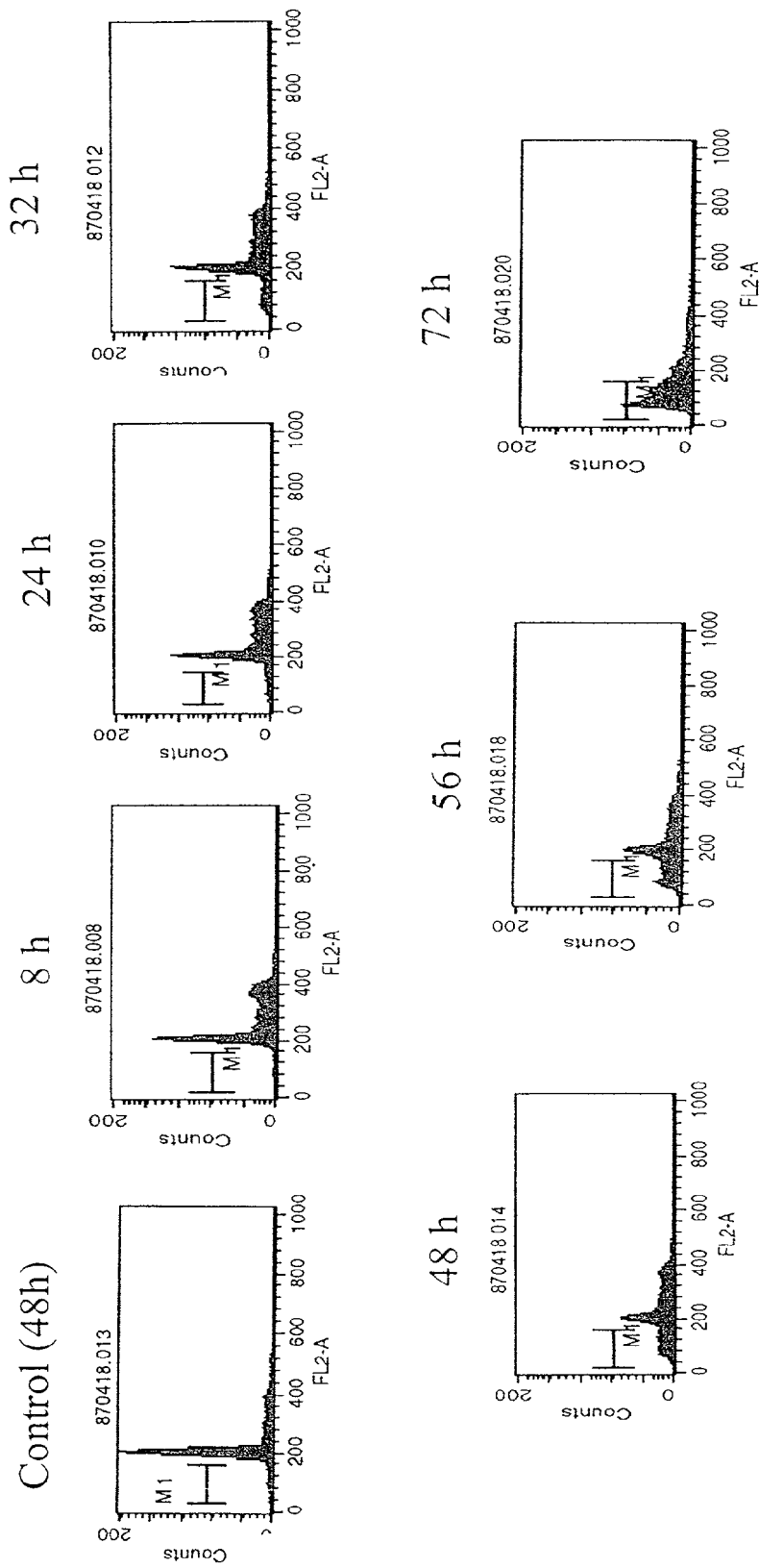

FIG. 6. Flow cytometry analysis of the DNA content in normal and apoptotic MCF-7 cells as a function of treatment time.

MCF-7 cells were incubated in RPMI 1640 medium spiked either with 0.4% DMSO (vehicle) or 1 mg/ml EA fraction of *A. formosanus*, and then harvested at indicated time points. M1 denotes the apoptotic peak and the image analyzer generated percent of apoptotic cells.

Figure 7:
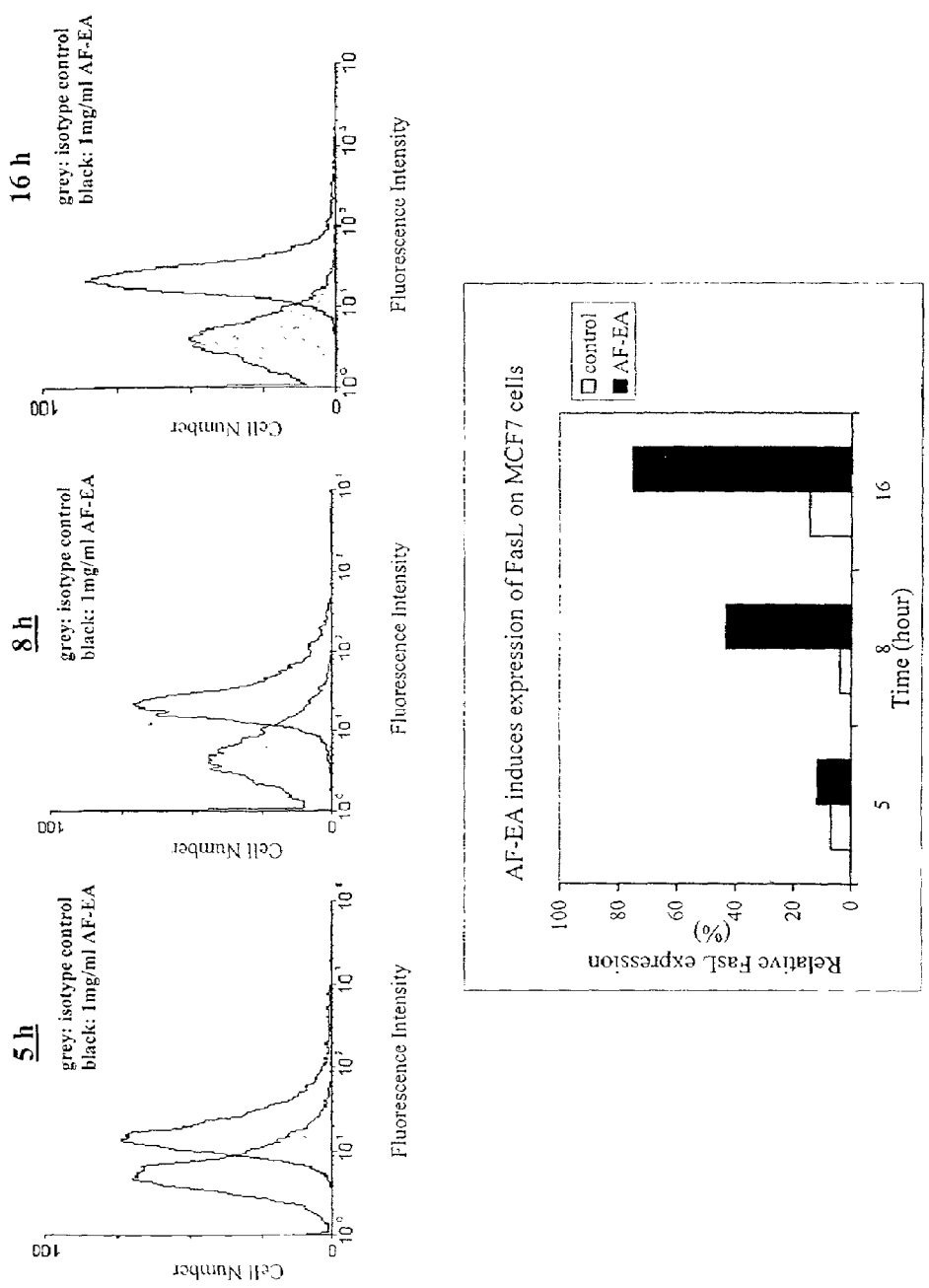

FIG. 7. Effect of the EA fraction of *A. formosanus* on inducing cell surface expression of FasL activities on MCF7 cells. MCF7 cells were exposed for 5, 8 or 16 hours, respectively, to 1 mg/ml EA extract or 0.4% DMSO solution (vehicle control).

FasL expression was determined by flow cytometry analysis using a mouse anti-human FasL IgG, clone NOK-1, or isotype control mouse IgG, MOPC-21, and a FITC-conjugated rat anti-mouse IgG for secondary staining. The results were analyzed by a Coulter EPICS XL flow cytometer (Beckman Coulter, USA) using the Expo XL 4 Cytometer software.

FIG. 8. Protein expression profile of caspases 7, 8, and 9, cytochrome c, NF-κB, actin (A), and poly-ADP-ribose-polymerase (PARP) (B) in MCF-7 cells treated without (control) or with the EA fraction of *A. formosanus*.

Aliquots of comparable cell lysates containing 40 μg of proteins of MCF-7 tumor cells treated with or without test plant extract were subjected to a 5–20% SDS gradient gel electrophoresis. After electro-transblotting proteins in SDS gel onto a PVDF membrane, specific protein bands reacted with test primary antibodies and then treated with horse radish peroxidase (HRP)-conjugated secondary antibodies at room temperature for 1 h. The reacted protein bands were visualized by calorimetric method.

FIG. 9. In vivo inhibition of B16 melanoma tumor growth in CS7BL/6J mouse model by plant extract (AH-sup) of *A. formosanus*.

Various administrating methods of plant extracts into test mice, including intraperitoneal (i.p.), intratumoral (i.t.), and oral force-feeding, were employed for this experiment. Mice administered with phosphate buffer only via i.p. injection (control 1), or via force-feeding and i.p. injection concomitantly (control 2) were used as controls. Seven mice per group were used for each experiment.

FIG. 10. The chemical fingerprints and the candidate index compounds of the AH-sup (A) and EA fraction (B) of *A. formosanus*.

Panel A: Metabolite profiling of the three different preparations of AH-sup extract from *Anoectochilus formosanus* plant. The three chromatograms were obtained from a C-18 reverse phase HPLC system, and the structures and identities of eight indexing compounds for composition profiling of the mixtures of phyto-compounds were identified using IR, mass and NMR spectrometric analyses. Compounds 1: Nicotinic amide; 2: adenosine; 3: cytosine; 4: isorhamnetin 3,4'-O-β-D-diglucopyranoside; 5: isorhamnetin 3-O-β-D-glucopyranoside; 6: caffeic acid; 7: (6R, 9S)-hydroxy-megastima-4,7-diene-3-one-9-O-β-D-glucopyranoside; and 8: kinsenone.

Panel B represents a chromatogram of the EA fraction from *Anoectochilus formosanus* plant extract, as obtained from a Si-60 HPLC system. The candidate compounds to serve for indexing or referencing in EA fraction are: 1: long chain aliphatic acid; 2: α-amyrin trans-p-hydroxy cinamate; 3:α-amyrin cis-p-hydroxy cinamate; 4: isorhamnetin; 5: kinsenone; 6: p-hydroxybenzyl alcohol.

Figure 11:
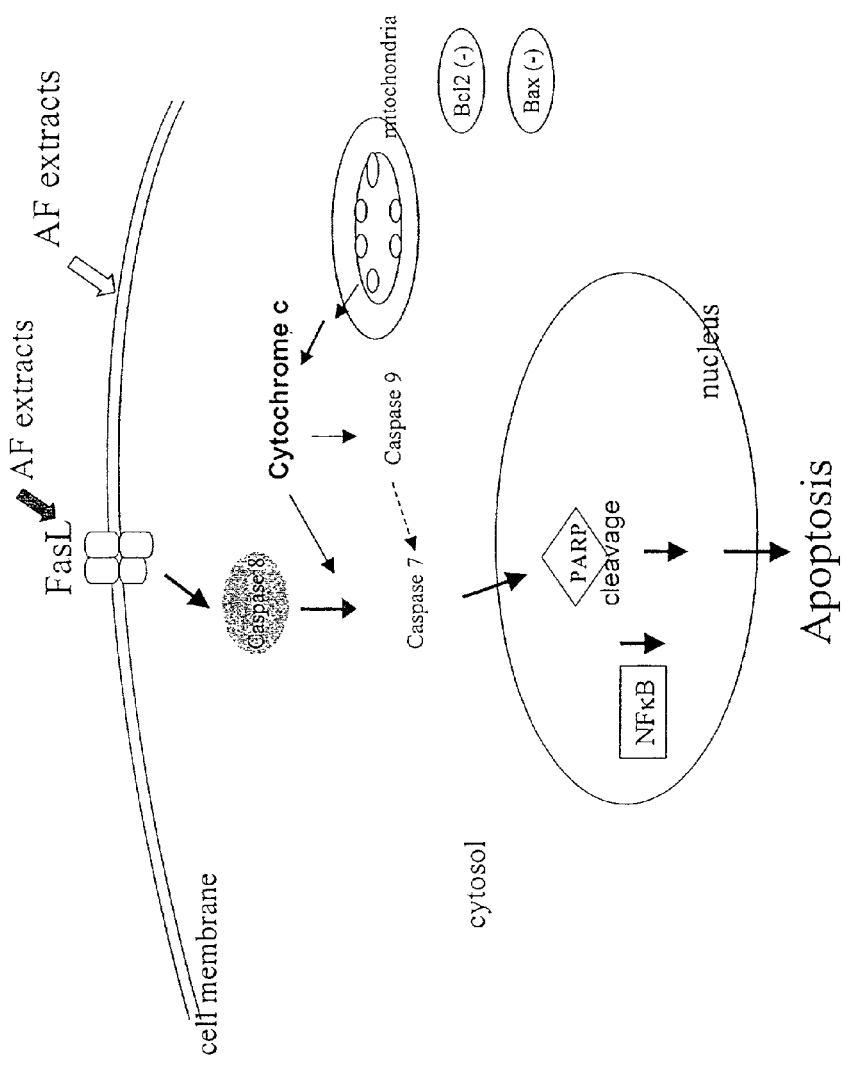
Figure 11:
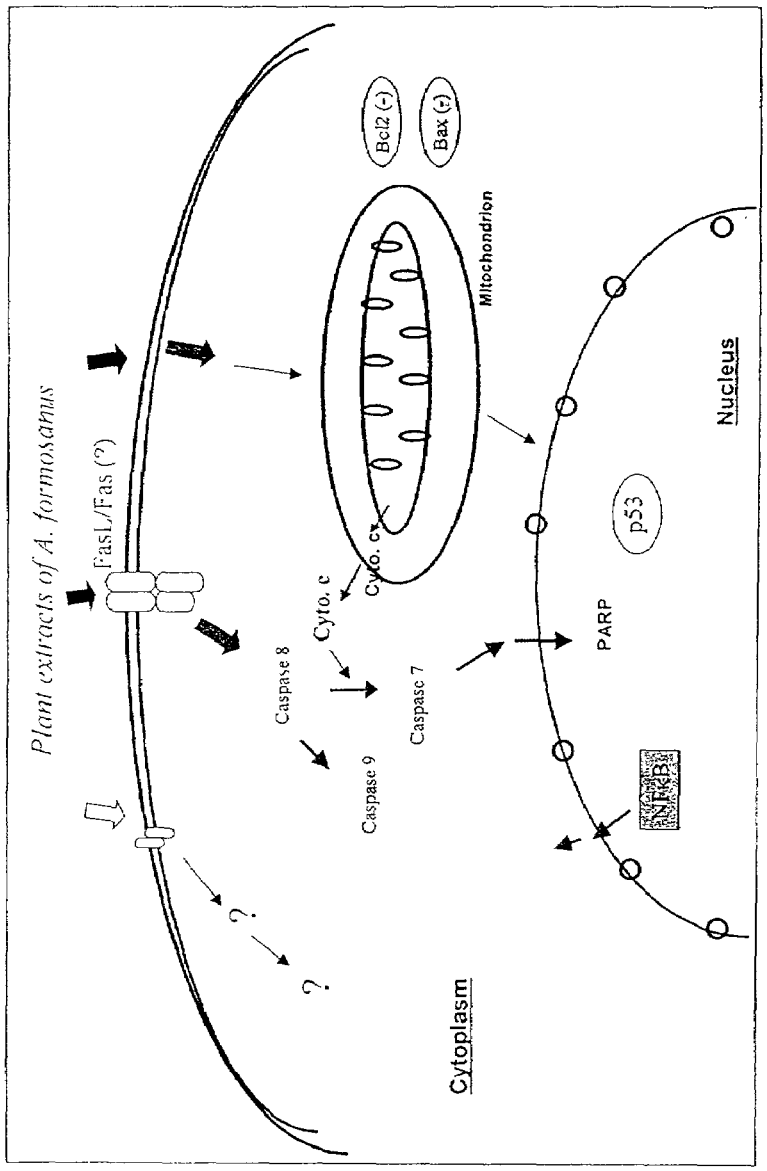

FIG. 11. A proposed signaling pathway of apoptosis in MCF7 tumor and human mammary tumor cells induced by plant extract of *A. formosanus*.

DETAILED DESCRIPTION OF THE PREFERRED EMBODIMENT

We adapted the anti-tumor drug-screening strategy developed at the NCI (Monks et al., 1991) with some modifications, primarily aimed at evaluating specific cytotoxicity on tumor cells by *A. formosanus* plant extracts. We employed a defined and reproducible "bioactivity-guided fractionation strategy and protocol" to evaluate the potential anti-tumor cell effects of the *A. formosanus* total plant extracts and the bio-organically derived fractions. The mechanism-specific cytotoxic activity on tumor cells obtained from specific plant extracts of *A. formosanus* is apparently involved in the induction of apoptosis, as evaluated using flow cytometry, western-blot analysis, and caspase(s) activity assays. These findings are very similar to various published studies demonstrating the apotitic effects induced by specific anti-cancer drugs. See for instance the published studies of Whllie et al., 1980 and Jiang et al., 1996).

1. Anti-Cell Proliferation Assay

B 16, MCF-7, and HepG2 cells were grown in ATCC-recommended culture media, containing 10% fetal bovine serum, 100 U/ml penicillin, and 100 µg/ml streptomycin as supplements. RPMI 1640 (Gibco BRL, USA) was used to grow B16 and MCF-7 cells, and Minimum Essential Medium (MEM, Gibco BRL, USA) for HepG2 cells.

The effect of *A. formosanus* plant extracts and the derived fractions on growth of target tumor cells was mainly evaluated by using MTT colorimetric assay as described elsewhere (Mosmann, 1983) with minor modifications. The tetrazolium ring of MTT (which confers a yellow color) is cleaved by mitochondrial dehydrogenase in living cells, and this produces the brown colored formazan precipitates. The relative absorbance changes at 570 nm are then measured. For MTT assays, target tumor cells ($5 \times 10^3$ to $1 \times 10^4$) were incubated with or without plant extracts in 96 well titer plates for 1 to 3 days. After incubation, adherent cells were washed once with fresh medium, and MTT dye (0.5 mg/ml in PBS) was then added into the corresponding cell culture medium as described above, and reactions allowed to be carried out at 37° C. for 4 hours. The insoluble reaction product was then collected by centrifugation, dissolved in 100 µL of DMSO, and incubated at 37° C. for 2 hours. All assays were performed in quadruplicate cell sets. The cell proliferation-inhibition effect was expressed as the relative absorption at 570 nm using a microplate reader (Labsystems Multiskan MS, Finland). The percentage of cell survival after treatment with plant extracts was calculated using the following formula: viable cell number (%) $OD_{570}$ (treated cell culture)/$OD_{570}$ (control (un-treated) cell culture)$\times 100\%$. For certain test cells, a $^3$H-thymidine incorporation assay was also employed to determine the anti-cell proliferation activity in plant extracts of *A. formosanus*, by following the stringent experimental protocol, as described by Seufferlein and Rozengurt (1995).

2. Fluorescent Microscopy Analysis and Flow Cytometry Analysis of Tumor Cells The Apoalert Annexin V-EGFP method (CLONTECH, Palo Alto, Calif.) was used to assess for apoptosis in test cells (Zhang et al., 1997). MCF-7 tumor cells were treated for 4 hours with EA fraction (1 mg/ml) or the vehicle (0.1% DMSO), washed with fixing solution, and stained with Annexin V-EGFP and/or propidium iodide for 15 min in dark. Cells were viewed using a Nikon ECLIPSE E800 inverted fluorescentscope.

Test tumor cells ($1 \times 10^6$ cells), with or without treatment using the evaluating plant extracts or the derived phytochemicals, were harvested and fixed with 1 ml ice-cold, 70% ethanol at 4° C. for 2 hr. Cellular DNA was stained for 30 minutes in the dark with PI staining solution containing 50 µg/ml propidium iodide (PI) and 100 µg/ml RNase A in PBS buffer. The percentage of cells with a sub-G 1 DNA content over total DNA was taken as a measure of the apoptotic cell population using a Coulter EPICS XL flow cytometer (Beckman Coulter, USA). Data were generated from samples with at least 10,000 cells per assay and analyzed with the DNA MultiCycle program (Beckman Coulter, USA).

3. Induction of FasL Expression on MCF7 Cells and Flow Cytometry Analysis of FasL Expression Aliquots of $1 \times 10^6$/ml cells were cultured for overnight in six-well flat-bottom plates in RPMI 1640 medium supplemented with 10% heat inactivated fetal bovine serum. EA plant extract (1 mg/ml) or 0.4% DMSO was then added to growth media and incubated for 5.8 or 16 hours. After treatment, cells were harvested using 0.5 ml/well Trypsin/EDTA and washed twice in phosphate buffered saline (PBS), pH 7.2.

Aliquots of $5 \times 10^5$ cells in a final volume of 100 µl each PBS were incubated for 30 min at 20° C. with 1 µg mouse anti-human FasL IgG1, clone NOK-1 (Pharmingen, USA), washed once, and resuspended in 100 µl PBS. A mouse IgG1, clone MOPC-21 (Pharmingen, USA) was used as isotype control. For secondary staining, cells were incubated for 30 min at 20° C. in the dark with 1 µg FITC-conjugated rate anti-mouse IgG, clone LO-MG1–15 (Biosource, California, USA), and washed twice in PBS prior to analysis by a Coulter EPICS XL flow cytometer (Beckman Coulter, USA) using the Expo XL 4 Cytometer software.

4. Western Blot Analysis

Test cells ($2 \times 10^6$) were washed with PBS once and lysed in 100 µL lysis buffer (pH 7.0, 20 mM PIPES, 10 mM NaCl, 1 mM EDTA, 0.1% CHAPS, 10% sucrose, 10 mM DTT, 5 mM HEPES, 0.05% (v/v) Triton X-100, 1 mM $MgCl_2$, 2.5 mM EGTA, and 0.438% (w/v) β-glycerol-phosphate) and 2 µL protease inhibitor cocktail set III (Calbiochem Co., USA) for 20 minutes on ice, and vortex-mixed every 5 minutes. PIPES, CHAPS and HEPES chemicals were purchased from Sigma Chemical Co. (MO, USA). After centrifugation, protein concentration in the supernatant was determined as described by Bradford (1976), using bovine serum albumin as a standard. Aliquots of 40 µg of protein were separated on a 5–20% gradient mini-SDS-polyacrylamide gel (Laemmli, 1970), and then transferred onto a PVDF membrane (Millipore). PVDF filters were blocked for non-specific binding with 3% non-fat dry milk in TBS buffer (10 mM Tris, pH 7.5 and 100 mM NaCl), and probed with specific primary antibodies in blocking solution at 4° C. overnight with agitation. Rabbit anti-actin (Oncogene Research Products), mouse anti-PARP (Related Products), mouse anti-cytochrome c (Pharmingen), rabbit anti-NF-κB (Oncogene Research Products), mouse anti-porcaspases-2, -7, and -9 and anti-porcaspase-8 (BD Research Products) were used as primary antibodies. After washing with TBST buffer (0.1% Tween 20 in TBS buffer), blotting membrane was treated with alkaline phosphatase-conjugated secondary antibodies at room temperature for 3 h. The reacted protein bands were visualized by colorimetric method or by an enhanced chemiluminescence system (ECL, Amersham Pharmacia Biotech Co., UK) for image analysis on Kodak Biomax MS films (Eastman Kodak Company, USA).

5. Inhibition of B16 Tumor Growth in C57BL/6J Mouse

The animal tumor system employed was the mouse strain C57BL/6J, or often called C57 or B6 mouse system harbored with murine B-16 melanoma cells. Possible in vivo effects of *Anoectochilus formosanus* plant extract on tumor growth were evaluated in vivo using a moderate tumor cell load of B16 melanoma cells inoculated and grown in 2–3 month old test mice.

Five groups of mice, each with 7 mice per test group, were employed. A total of $1 \times 10^5$ B-16 tumor cells suspended in 50 µl of phosphate buffered saline (PBS) was implanted into the dermal tissue (intra-dermally) of the right abdominal area of each mouse on day 0. Three sets of mice were tested for the AH-sup treatment, by intra-peritoneal (i.p.) or intra-tumoral (i.t.) injections of test plant extracts, or by the force-feeding (f.f.) mode for testing anti-tumor effects. Specifically, from day 2 on, test mice in group 1 received PBS only via i.p. injection (control 1), and group 2 mice were treated with PBS only via force-feeding and i.p. injection concomitantly (control 2). Groups 3, 4 and 5 mice were treated with AH-sup solution by i.t. injection, i.p. injection, and force-feeding by mouth, respectively.

The injection dosage received by each test mouse was 1 mg of AH-sup in 100 µl PBS per day, while the force-fed mice took 2 mg in 200 µl per day orally. Both test groups were treated for 7 consecutive days after inoculation of tumor cells. Starting on day 8, the frequency of the treatment was changed to a slower pace, by treating mice every two days until day 21. In the case of force-feeding, the relative herb dosage tested in mice was equivalent to the ingestion or uptake of a 50 kg person drinking two servings of instant herb tea powders (2 tea bags) made from about 30 g of dried *A. formosanus* plant.

6. Metabolite Profiling and the Index or Composition Compound Analysis of AH-sup and EA Fractions of *Anoectochilus formosanus*

Analytical high performance liquid chromatographic (HPLC) analyses were performed using a Waters HPLC system equipped with a Waters 600 controller, Waters Delta 600 pump, and 2487 Duel λ absorbance detector. A 5 µm C-18 column (250×10 nm, Merck, Germany) was employed for the analysis of AH-sup fraction with two solvent systems, methanol-water (90:10, v/v) (A) and methanol (B). The elution conditions were performed as follows: 0 to 5 minutes, 80% A to B (isocratic); 5 to 30 minutes, 80–0% A to B (linear gradient); 30 to 60 minutes, 100% B (isocratic). The detector wavelength was set at 254 nm. A 5 µm Si-60 column (250×10 nm Merck, Germany) was employed for the FA active fraction with two solvent systems, n-haxane (A) and ethyl acetate (B). The elution gradient profile was performed as follows: 0–5 min, 70% A to B (isocratic); 5–15 min, 70–30% A to B (linear gradient); 15–20 min, 30% A to B (isocratic); 20–30 min 30%–0% A to B, the flow rate was 5 ml/min, and the detector wavelength was set at 280 nm. The structures of compounds 1 to 8 in the All-sup fraction and compounds 1 to 6 in the EA fraction were then elucidated using various spectroscopic analyses. UV spectra of test compounds were recorded with a Jasco V-550 spectrometer, and IR spectra obtained from a Bio-Rad FTS-40 spectrophotometer. Electron-impact mass spectrometry (EIMS) and high resolution electron-impact mass spectrometry (HREIMS) data were collected with a Finnigan MAT-958 mass spectrometer, and the NMR spectra recorded with Bruker Avance 500 and 300 MHz FT-NMR spectrometers, at 500 MHz ($^1$H) and 75 MHz ($^{13}$C).

Quantification of the content of index compound in EA fraction was done by a HPLC analysis using a known concentration of EA fraction. Individual peak area corresponding to index compound in the HPLC profile (metabolite profile) of the EA fraction was determine at the observed maximal absorbance of $OD_{280}$. The standard calibration curves (peak areas vs. concentrations) of the compounds, ranging from 0.05 to 1 mg/ml, revealed good linearity and $R^2$ values (>0.98). Quantification of the content of index compound in EA fraction was done by a HPLC analysis using a known concentration of EA fraction, and the peak area of specific compound was then determined and referred to their contents in the extract based on the standard calibration curve.

7. Preparation and Fractionation of *A. formosanus* Plant Extracts

Fresh plants of *A. formosanus* were purchased from a reputable Anoectochilus Cultural Station and the plants' identity and authenticity were validated by the specific morphological and anatomical features of the flowers (Lin et al., 1978).

Fresh (1000 g) or dried (100 g) whole plants of *A. formosanus,* including leaf, stem, and root tissues, were homogenized by grinding with a mortar and pestle, and extracted by a slow and steady boiling (about 100° C.) process for one hour with three volumes of distilled water. The extraction procedure described above was then repeated once. The supernatants from this two time extractions were collected by centrifugation at 24,000×g for 20 minutes at 25° C., and then lyophilized to dryness using a lyophilizer (LABCONCO, USA). This preparation gave rise to the total AF-Hot crude extract (ca. 49 g in dry weight). This AF-Hot extract was dissolved in phosphate buffer saline (PBS) and employed for anti-cell proliferation activity on target tumor cells. A defined "bioactivity-guided fractionation strategy and protocol" was employed for further fractionation of the AF-Hot of *A. formosanus,* as described in FIG. 1 and discussed above.

Figure 1:
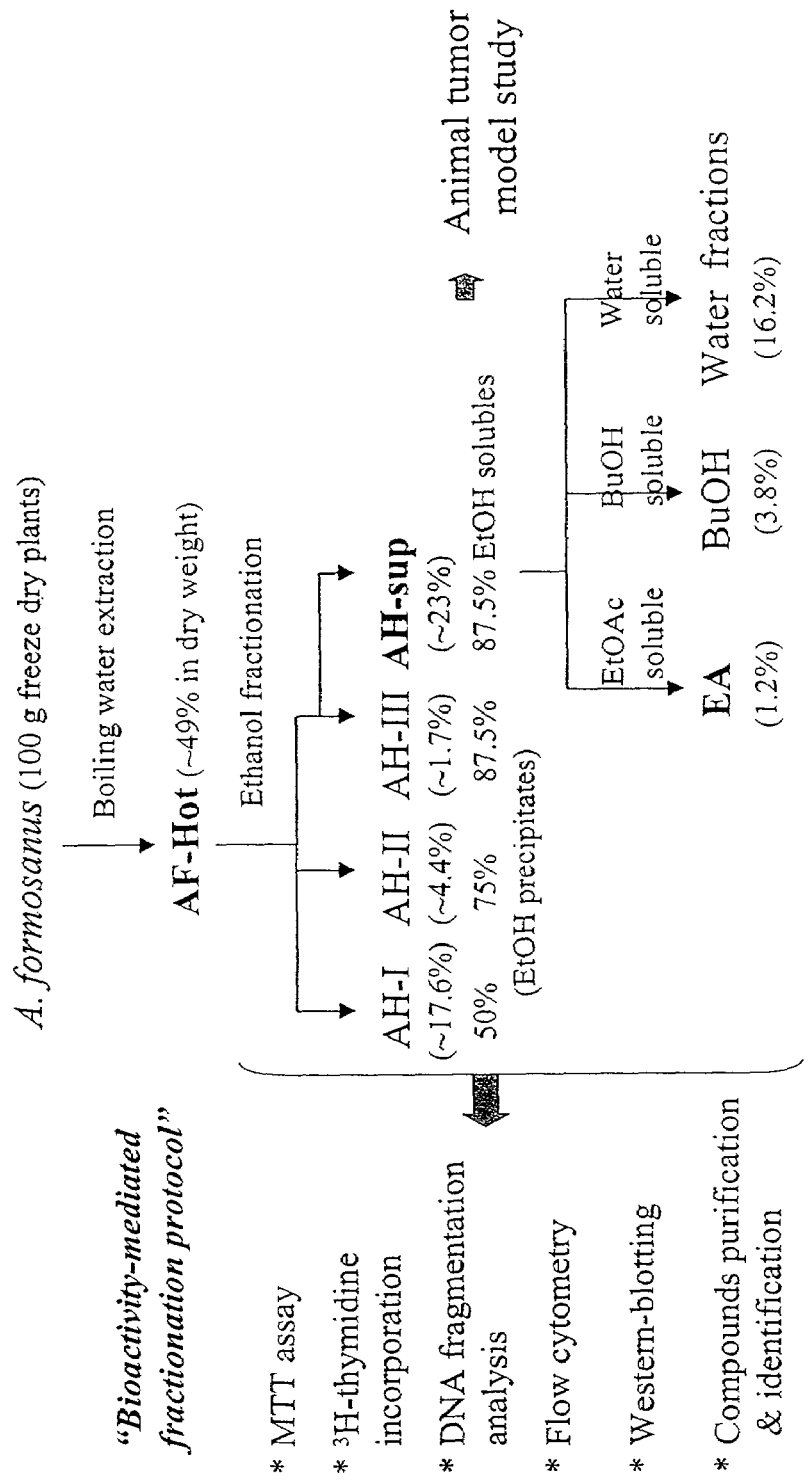
FIG. 1. Extraction protocol for preparation of total and fractionated plant extracts of *A. formosanus*.
This protocol in principle followed a "bioactivity-guided fractionation strategy" where the anti-tumor related bioactivity experimental systems were performed in accordance with the flow chart of an effective extraction and fractionation procedure for *A. formosanus* (AF).

Various sub-fractions were obtained from the AF-Hot crude extract using a stepwise ethanol fractionation procedure. AH-I, II, and III fractions were the ethanol-precipitated materials derived from the AF-Hot samples that were sequentially extracted organically with 50%, 75%, and 87.5% (v/v) ethanol, respectively, and the AH-sup was the remaining soluble form/fraction of the AF-Hot sample treated with 87.5% ethanol. In summary, equal volume of anhydrous ethanol was slowly added into the AF-Hot crude extract with stirring and allowed to stand at room temperature for 30 minutes. The AH-I fraction (~17.6% in dry weight) was collected from the pellet by centrifugation at 24,000×g for 20 min at 4° C., and the supernatant was then further added with anhydrous ethanol to reach a final ethanol concentration of 75% (v/v) by using the same procedure as described in preparation of AH-I fraction. In this step, AH-II fraction (~4.4% in dry weight of the original plant materials) was obtained. The AH-III (~1.7% in dry weight) and AH-sup (~23% in dry weight) fractions were obtained from the 87.5% (v/v) ethanol precipitates and the soluble fraction, respectively. A further fractionation procedure on the All-sup (19.3 g) was then subjected to differential solvent partitioning using ethyl acetate (EA) and followed by butanol (BuOH) to yield the EA (about 1.2 g), BuOH (about 3.4 g), and water (14.4 g) subfractions, respectively (FIG. 1). In these organic solvent fractionation steps, ethyl acetate was mixed vigorously with AF-sup at an equal volume (1:1) and allowed to stand at room temperature until a separated and clear organic EA and aqueous layers were obtained. The EA fraction was then collected and the aqueous layer was extracted again with ethyl acetate. The two EA fractions were pooled and evaporated to dryness using a rotavaper. The aqueous layer was then further extracted with butanol using the same procedures as was performed for the ethyl acetate extraction, yielding the BuOH and water subfractions. The AF-Hot, AH-I, AH-II, AH-II and AH-sup fractions thus obtained were dissolved in phosphate buffered saline (PBS), and the EA, BuOH and Water fractions were dissolved in dimethyl sulfuric oxide (DMSO) solvent for subsequent use in the following experiments.

Cytotoxicity Analysis

MTT (tetrazolium) assay (Mosmamn, 1983), a calorimetric assay for measuring various dehydrogenase activity in mitochondria of living cells, and $^3$H-thymidine incorporation assay, for measuring DNA synthesis in viable cells, were employed for evaluation of anti-tumor cell activity. Three typical tumor cell lines, i.e., human mammary tumor (MCF-7), mouse melanoma (B16), and human hepatoma (HepG2), were used in the same or parallel tests.

Figure 2:
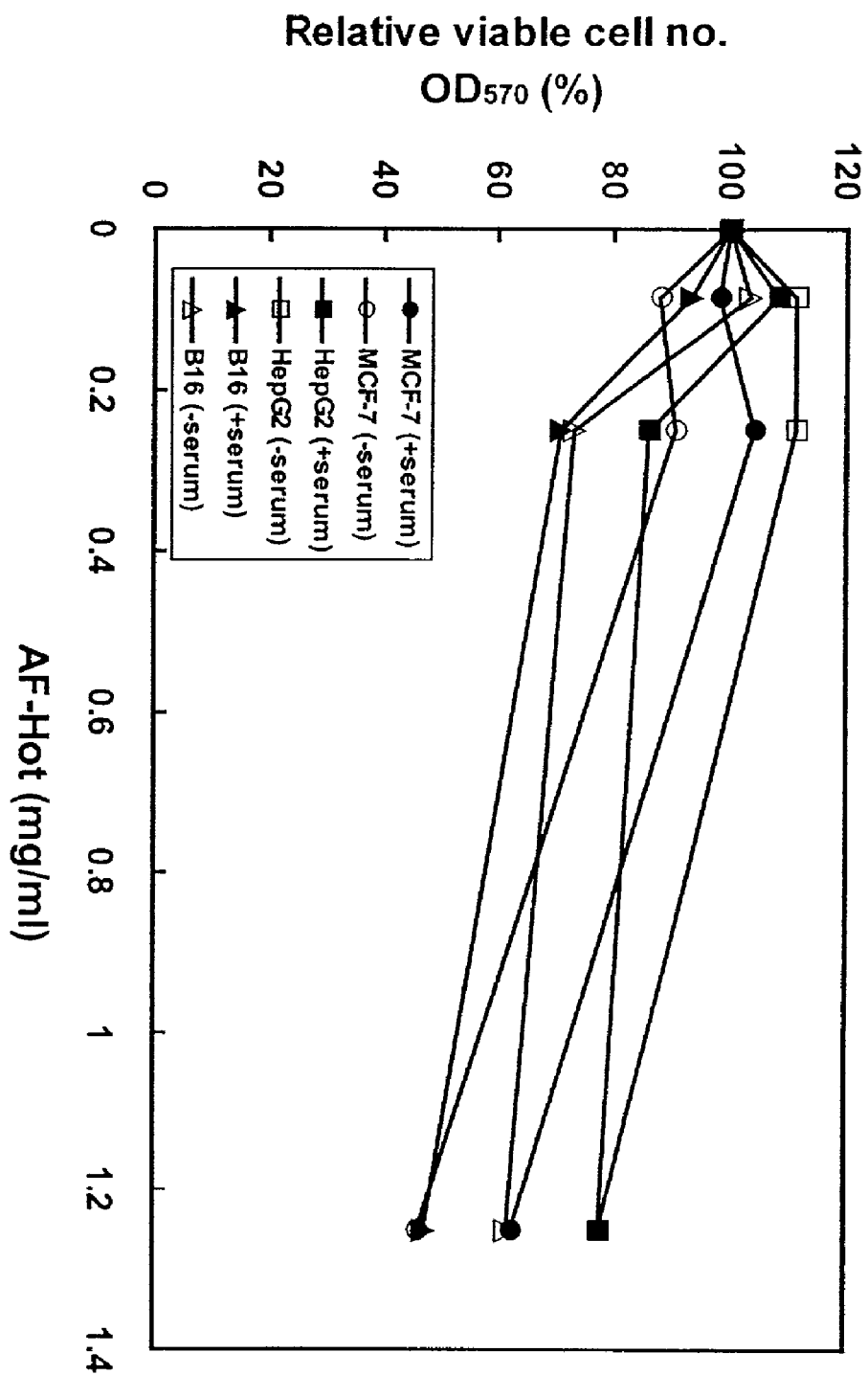
FIG. 2. Anti-tumor cell proliferation effect of AF-Hot extract of *A. formosanus* on MCF-7 human mammary adenocarcinoma, HepG2 human hepatoma, and mouse B16 melanoma cell lines in growth media containing with or without fetal bovine serum.

FIG. 2 shows the cytotoxic effect of AF-Hot on the MCF-7, HepG2, and B16 tumor cells in the presence or absence of fetal bovine serum in growth medium of test tumor cell cultures. A very similar level of anti-tumor cell effect was observed for total plant extract AF-Hot regardless of whether the culture medium was supplemented with or without fetal bovine serum. This is a useful and important baseline information, demonstrating that the potential interference between fetal bovine serum components and test plant extracts apparently does not play a role in the anti-tumor cell proliferation activity as conferred by plant extracts of A. formosanus. The total crude extract (AH-Hot) prepared from two different sets of starting plant materials were observed to confer similar or comparable trends of cytotoxic effects on test tumor cells (data not shown). Based on MTT assays, the AH-sup sample showed the most significant cytotoxic or anti-proliferation effect on MCF-7, B16, and HepG2 cells, as compared to those conferred individually by the AH-I, AH-II, and AH-III fractions derived from the AF-Hot total plant extract. Less than 45 to 55% of tested cells were detected as viable for MCF-7, HepG2, and B16 tumor cells when they were treated with AH-sup a dosage of 1.5 mg/ml for 48 hours. Whereas, more than 80% viable tumor cells were observed when all three tumor cell lines were treated with the same dose of AH-I, AH-II, or AH-III fractions. A similar trend of cytotoxic effects of AF-Hot and AH-sup was also observed when the test tumor cells were evaluated by $^3$H-thymidine incorporation assays. The relative effects on cytotoxicities (or anti-tumor cell activity) of the total crude extract (AH-Hot), AH-sup, EA, BuOH, and Water fractions were further characterized and compared using MTT assays.

As shown in FIG. 3, the EA fraction conferred the highest levels of cytotoxic effect on all tested cell lines, as compared to the AF-Hot or other organic subfractions of A. formosanus extracts. Table 1 summarizes the effective dosage for 50% inhibition on cell proliferation ($ED_{50}$) of four different bio-organic subfractions (AH-sup, EA, BuOH, and Water) on MCF-7, B16, and HepG2 cells. The $ED_{50}$ of the EA fraction for MCF-7 human mammalian adenocarcinoma cells was detected at 0.08 mg/ml, and this is 10-fold less than that obtained for AH-sup subfraction.

Table I

Cytotoxicities of various organic solvent extracted subfractions of A. formosanus plant on three targeted human or mouse tumor cells

| Cells | $ED_{50}$ (mg/ml) | | | |
|---|---|---|---|---|
| | Sup | EA | BuOH | Water |
| MCF-7 | 0.86 | 0.08 | 1.5 | 2.70 |
| HepG2 | ND(>>1.5) | 0.09 | 0.23 | 2.50 |
| B16 | ~1.60 | 0.07 | >4 | ND(>>2.0) |

ND: Not detected at indicated dosage
$ED_{50}$ The effective dosage (ED) for inhibiting 50% of cell proliferation.

Light and Fluorescent Microscopic Analyses of Morphology and Culture Behavior of Test Tumor Cells Light microscopy analysis showed that the morphology of MCF-7 cells in culture had significantly altered after the treatment with plant extracts of A. formosanus. At a dose of 1 mg/ml, EA fraction exhibited the most significant effects on the morphological change of MCF-7 cells, as compared to that of AH-sup and AF-Hot treatment (FIG. 4). Similar results were also observed for the HepG2 and B 16 tumor cells (data not shown). These observations are in good consistence with the observed $ED_{50}$ values of these extract fractions as was represented in Table I. To further verify if the treated MCF-7 cells were progressing toward apoptosis, fluorescent microscopy analyses were performed using Annexin V-GFP and propidium iodide staining. FIG. 5 shows that an early redistribution of plasma membrane phosphatidylserine was readily detected in MCF-7 cells after treatment with EA fraction for four hours. This result shows that EA fraction has effectively induced apoptosis on MCF-7 cells.

Flow Cytometry Analysis

FIG. 6 shows the flow cytometric profiling of the change of DNA content and cell cycle behaviors of MCF-7 cells, as a function of time by treatment with the EA fraction. Approximately a level of 48% of apoptotic DNA level (as determined from the sub-G1 peak) was obtained for MCF-7 cells post treatment with EA fraction (0.25 to 1 mg/ml) for 48 hours, and this apoptotic DNA level was increased to 71% at the 72 hours post treatment. Under the same experimental conditions, similar DNA profiles were detected in HepG2 cells compared to that of MCF-7 cells, whereas approximately 72% apoptotic DNA level was already detected in B16 cells at the 48 hours treatment. AH-sup fraction (6 mg/ml) of A. formosanus also exhibited a similar effect on the DNA content and cell cycle behaviors of MCF-7 and B16 cells (data not shown). These results show that the cytotoxic effect of A. formosanus on test tumor cells is likely mediated via the process of programmed cell death or apoptosis (Williams, 1991).

EA Extract Induces FasL Expression on MCF-7 Cells

It is known that expression of Fas ligand (FasL) can mediate apoptosis by binding to its cognate receptor Fas (Naujokat et al., 1999). In this study, flow cytometry analyses using a specific anti-human FasL IgG1 conjugated with fluorophore (FITC) was employed to evaluate whether the observed apoptosis of MCF-7 induced by EA extract of A. formosanus was triggered by the expression of FasL. As shown in FIG. 7, the expression of FasL protein was increased drastically from 10% to 76%, relative to the non-treated control MCF-7 cells, when the tumor cells were treated with the EA fraction from 5 hours to 16 hours in culture (FIGS. 7A&B).

Western-Blot Analysis

Figure 8A:
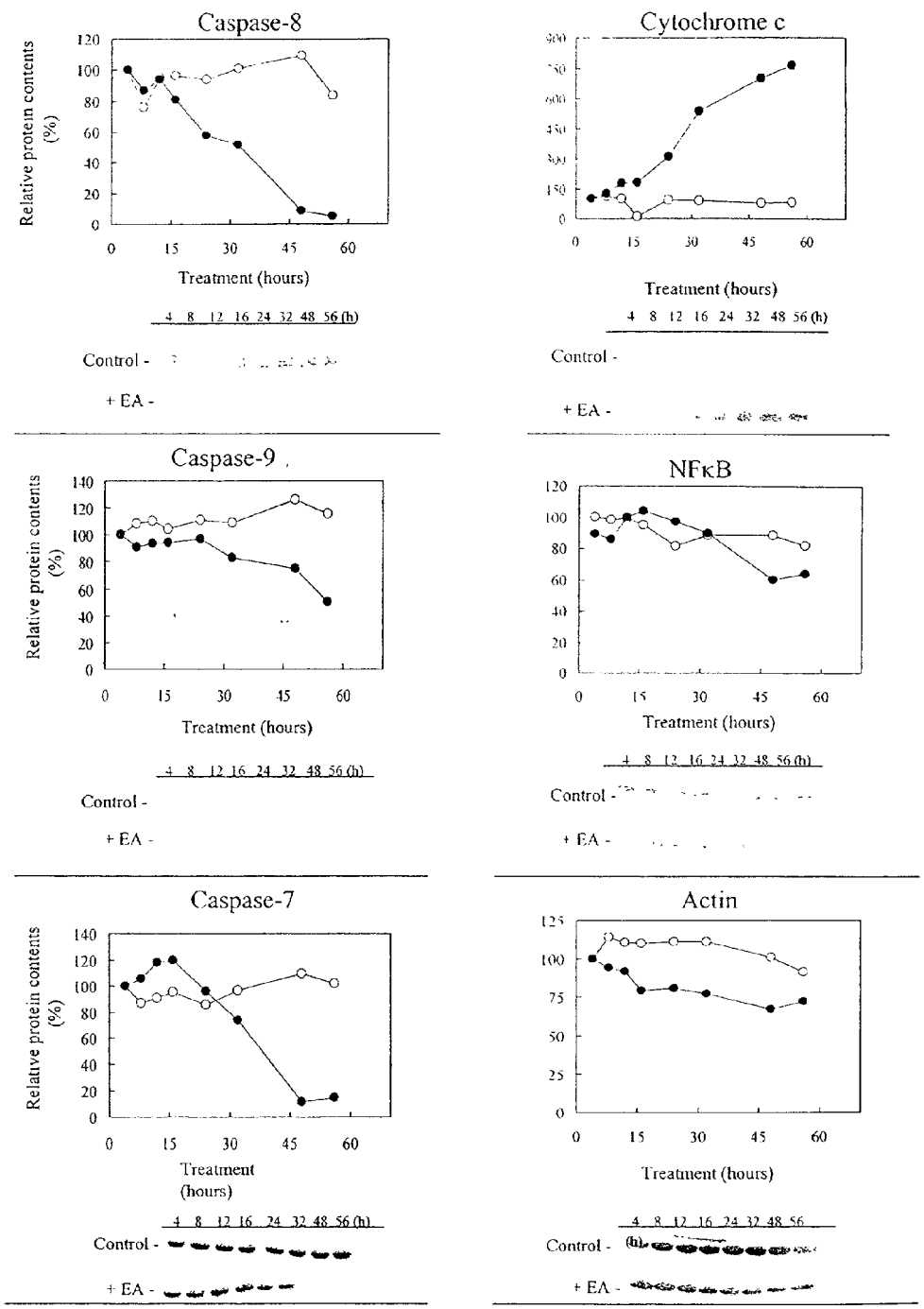
Figure 8B:
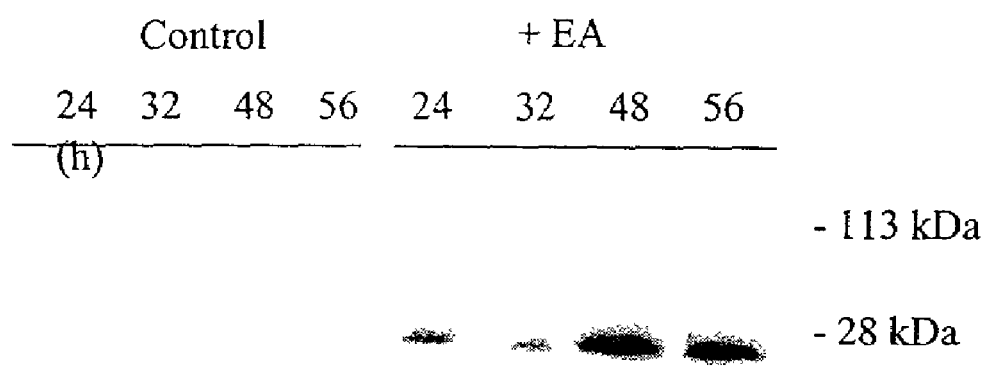

Several single compound drugs exhibiting anti-tumor activities, including Taxol and etoposide, have been demonstrated to cause mitochondrial damage and content release, resulting in cytosolic accumulation of cytochrome c (Fang et al., 1998). We have evaluated the possible effects of A. Formosanus plant extracts on release of mitochondria cytochrome c into cytosol of test tumor cells. FIG. 8 shows that a significant increase of the cytosolic cytochrome c levels in MCF-7 cells was observed when treated with EA (or AH-sup) fraction of A. formosanus plant extracts. Caspase proteases have been shown to drive apoptotic signaling and execution by cleaving critical cellular proteins specifically and solely after the aspartate residues (Wolf and Green, 1999). Caspases exist as latent zymogens, however, once activated by apoptotic signals, the pro-caspases are proteolytically cleavaged and begin to take action. The activated apoptotic initiators (caspases-8 and -9) in turn can activate the executioner caspases (caspases-3, -6, and -7). In our study, pro-caspase-8 (~55 kDa) was found proteolytic cleavaged in MCF-7 cells after treatment with EA extract within approximately 16 hours (FIG. 8A). For the case of caspase-7 precursor protein, EA extract was detected to induce the proteolytic processing of caspase-7, starting at 24 to 32 hours post-treatment. Caspase-9, known to involve in the early activation cascade was also activated in EA-treated MCF-7 cells. Treatment of MCF-7 cells with EA extract have also resulted in a time-dependent proteolytic cleavage of poly (ADP-ribose) polymerase (PARP), another hallmark of apoptosis, with an accumulation of the 28 kDa and the concomitant disappearance of the full-size 116 kDa molecule (FIG. 8B). It has been previously reported that NF-κB activation can result in protection against TNF-α-induced apoptosis in HeLa cells, a cervical-cancer cell line, in vitro (Bursch et al., 1992). The Rel A subunit (p65) of NF-κB is known to be directly involved in the inhibition of apoptosis (Liu et al., 1996). In this study, after EA treatment there was detectable effect on the suppression of Rel A protein level in MCF-7 cells (FIG. 8A). Expression of the Rel A subunit in mouse B16 melanoma was significantly suppressed as a function of the treatment time period with AH-sup (6 mg/ml) or EA fraction (0.25–1.0 mg/ml) of A. formosanus (data not shown). A flux of caspase 3 activity, an increase from 4 to 24 hours and then a decrease from 24 to 48 hours, as a function of treatment time by AH-sup in B16 melanoma cells was observed (data not shown). These results indicate that specific apoptosis mechanisms are involved in the observed killing of targeted tumor cell lines, instead of general, non-specific chemical toxification or killing. On the basis of the results of flow cytometry, western-blot analysis, and caspase(s) activity assays, we proposed a possible mechanism for the apoptosis in MCF-7 tumor cells induced by the plant extract of A. formosanus (FIG. 11).

In Vivo Inhibition of B16 Tumor Growth in C57BL/6J Mouse Model

Suppression or retardation of in vivo tumor growth by A. formosanus plant extract in the CS7Bl/6J mouse tumor model was also demonstrated as another aspect of this invention. Three commonly used drug-administering methods, including intra-tumoral injection (group 3), intraperitoneal injection (group 4) and force-feeding via oral administration (group 5), were performed in parallel in this study. FIG. 9 summarizes the experimental results. In all three cases, test mice treated with the AH-sup fraction showed a significant delay of tumor growth, as observed at the early stage for in vivo tumor growth (between 6 to 10 days post treatment) (FIG. 9). The highest inhibitory effect on tumor growth was observed between 8 and 16 days post-tumor cell implantation. On day 17, all of the experimental test groups, including the i.t. injection, i.p. injection, and the force-feeding groups, have maintained with a set between 4 to 7 mice per group, with tumor size measured below 12 mm in diameter. In contrast, only 3 and 2 mice were with tumor size below 12 mm in the non-AH-sup treated, control 1 and control 2 groups, respectively; and 3 mice in control 2 groups were scarified due to overburden of tumor load (FIG. 9). On day 21, all surviving mice in both control groups had effectively grown tumors to more than the critical size limit of 15 mm tumor in diameter, legally allegeable for sacrificing as test mice according to Animal Room regulation rules. In contrast, at the same experimental stage of day 21 post-treatment, there were still 4 mice in group 3, two mice in group 4, and one mouse in group 5 that still have tumors exhibiting a size of smaller than 15 mm in diameter (data not shown). These results suggest that all of the three tested administration methods for delivery of herbal extracts can provide a significant level of anti-tumor effects, with the most remarkable results obtained from the group 3 mice that were i.p. injected with AH-sup fraction of A. formosanus. Specifically, an inhibition of more than 70% tumor growth in test mice was obtained when the animals were intra-tumorally administered with a plant extract of A. formosanus. Results from these experiments indicate that in vivo growth of B16 melanoma tumor in C57BL/6J mice can be effectively and readily inhibited by administration of the partially purified plant extracts of A. formosanus under the experimental conditions of this invention.

Figure 10A:
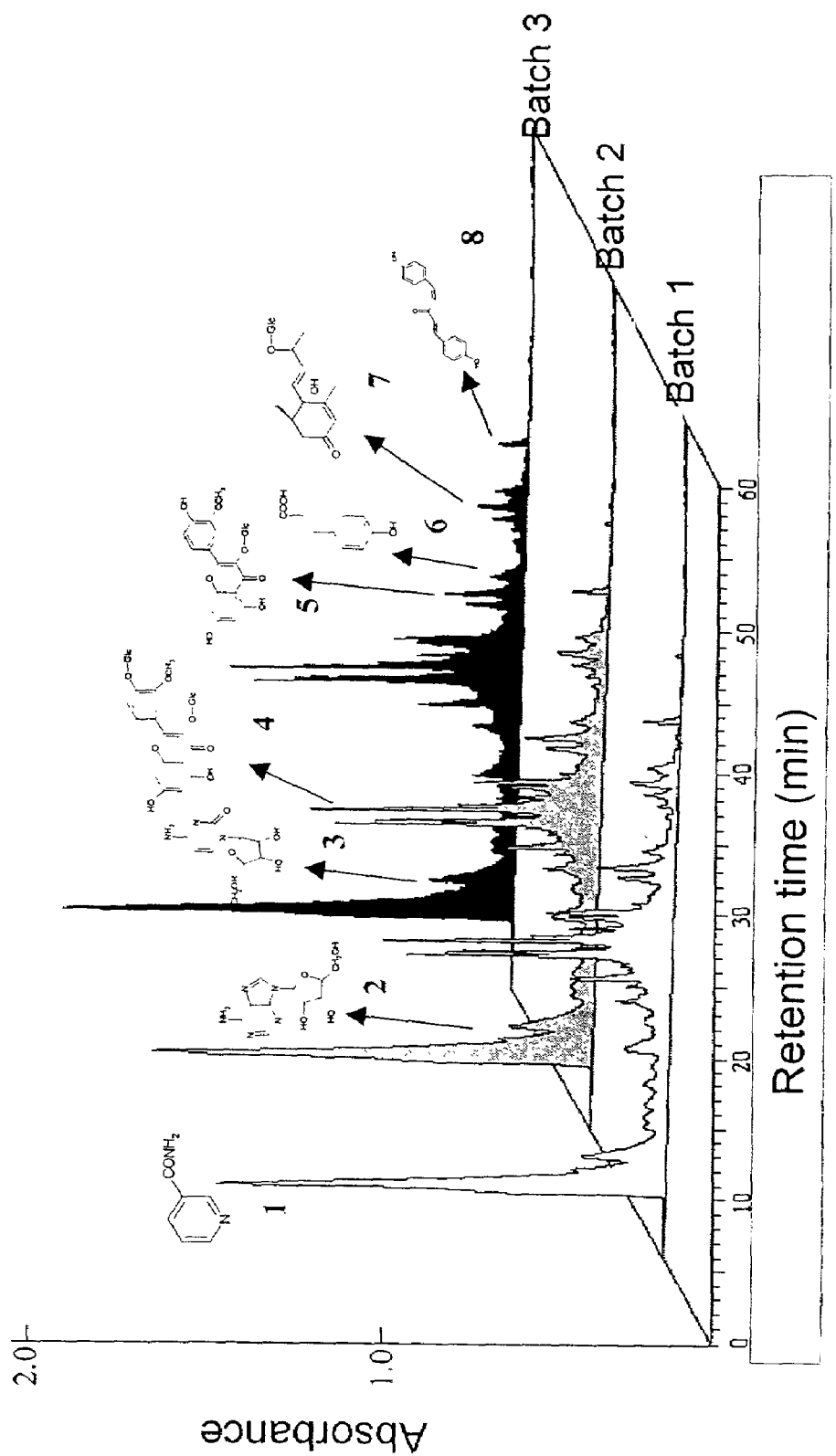

Chemical Fingerprinting Analysis and Index Compound Identification and Quantification Analytical high performance liquid chromatographic (HPLC) analyses were performed using a Waters HPLC system equipped with a Waters 600 controller, Waters Delta 600 pump, and 2487 Duel λ absorbance detector. The three chromatograms of AH-sup plant extract from Anoectochilus formosanus were obtained from a C-18 reverse phase HPLC system. The index compounds are herein to represent the defined chemical composition and/or characteristics of a mixture of relatively crude plant extract substances or phytochemicals. For the case of AH-sup, the eight candidate index compounds identified by using IR, mass and NMR spectrometric analyses are: Compounds 1: Nicotinic amide; 2: Adenosine; 3: Cytosine; 4: Isorhamnetin 3,4'-O-β-D-diglucopyranoside; 5: Isorhamnetin 3-O-β-D-glucopyranoside; 6: Caffeic acid; 7: (6R, 9S)-Hydroxy-megastima-4,7-diene-3-one-9-O-β-Dglucopyranoside; and 8: Kinsenone (FIG. 10A).

Figure 10B:
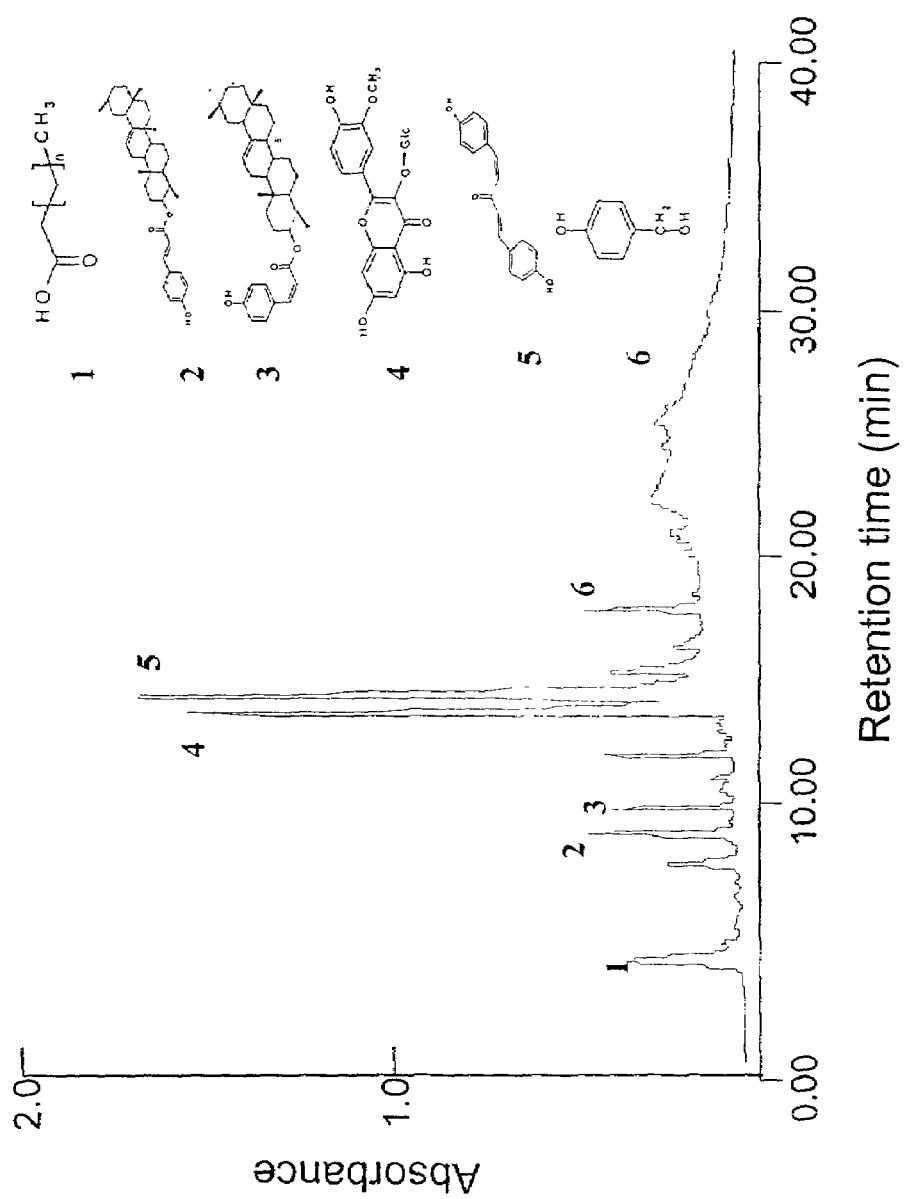

According to the results of MS and NMR analyses and by comparing with the spectral data with literatures (Wang et al, 2002; Ali et al., 1997), six compounds isolated from EA of A. formosanus were identified as long chain aliphatic acid (1; retention time (RT)=6.0 min). α-amyrin trans-p-hydroxy cinamate (2; RT=8.9 min), α-amyrin cis-p-hydroxy cinamate (3; RT=9.7 min), isorhamnetin (4; RT=13.5 min), kinsenone (5; RT=14.6 min), p-hydroxybenzyl alcohol (6; RT=18.0 min) (FIG. 10B).

Quantitative determination of the content of candidate index compounds 2 (Adenosine) and 5 (Isorhamnetin 3-O-β-D-glucopyranoside) in AH-sup fraction and candidate index compounds 2 (α-amyrin trans-p-hydroxy cinamate) and 4 (isorhamnetin) in EA fraction were characterized by analytical HPLC. Individual peak areas of the maximal UV absorbance corresponding to the candidate index compounds in the HPLC profile of AH-sup and EA fraction were monitored and determined. Calibration curves (peak area vs. concentrations) of the α-amyrin trans-p-hydroxy cinamate and isorhamnetin standards, ranging from 0.05 to 1 mg/ml, revealed a good linearity and $R^2$ values (>0.98) (data not shown). Quantification of the candidate index compounds in AH-sup and EA fraction was performed based on the known concentration of the specific fractions used for HPLC analysis, and the calculated amounts of peak areas of the candidate compounds corresponded well with the compounds revealed by our HPLC profiling analysis. Each gram of AH-sup fraction of *A. formosanus* contains 0.72 mg (0.072%) and 3.4 mg (0.34%) of adenosine and Isorhamnetin 3-O-β-D-glucopyranoside, respectively. EA extract of *A. formosanus* was found to contain 4.9 mg (0.49%) and 52.3 mg (5.23%) of α-amyrin trans-p-hydroxy cinamate and isorhamnetin, respectively in one gram of the extract.

The spectral data of adenosine and Isorhamnetin 3-O-β-D-glucopyranoside, α-amyrin trans-p-hydroxy cinamate, and isorhamnetin are summarized as follows:

Adenosine

Colorless needle crystal; mp 234–235° C.; EIMS for $C_{10}H_{13}N_5O_4$ found 274.2; $^1$HNMR (in $D_2O$): σ (ppm) 8.18 (1H, s), 8.08 (1H, s), 5.91 (1H, d, J=6.0 Hz), 4.28 (1H, dd, J=5.2, 3.0 Hz), 4.15 (1H, dd, J=5.2, 3.0 Hz), 3.78 (1H, d, J=1.5 Hz), 3.69 (1H, d, J=1.5 Hz).

Isorhamnetin 3-O-β-D-glucopyranoside

Yellow amorphous; mp 162° C.; EIMS for $C_{21}H_{20}O_{12}$ found 464.38; $^1$HNMR (in $D_2O$): σ (ppm) 7.96 (1H, d, J=2.0 Hz), 7.56 (1H, dd, J=8.0, 2.1 Hz), 7.04 (1H, d, J=7.8 Hz), 6.39 (1H, d, J=2.0 Hz), 6.20 (1H, d, J=2.0 Hz), 5.39 (1H, d, J=7.0), 3.72 (1H, dd, J=11.5, 2.0 Hz), 3.54 (1H, m), 3.44 (2H, m), 3.23 (1H, m).

α-amyrin trans-p-hydroxy Cinamate:

White solid; mp 105–106° C.; EIMS for $C_{29}H_{56}O_3$ found 572.43; $^1$HNMR ($CDCl_3$): σ (ppm) 7.62 (d, J=8.0), 7.45 (d, J=8.0), 6.85 (d, J=18.2), 6.32 (d, J=18.2), 5.22 (m), 4.70 (m), 1.17 (s), 1.01 (s), 1.00 (s), 0.96 (s), 0.90 (s), 0.89 (s), 0.86 (s).

Isorhamnetin:

Yellow amorphous; EIMS for $C_{16}H_{12}O_7$ found 312.6; $^1$HNMR ($CDCl_3$): σ (ppm) 7.96 (d, J=2.0), 7.56 (dd, J=8.0, 2.1), 7.04 (d, J=7.8), 6.39 (d, J=2.0), 6.20 (d, J=2.0).

REFERENCES

Al-Rubeai, M. (ed.) (1998) Apoptosis, Springer-Verlag Berlin Heidelberg, Germany.

Ahinad, N., Feyes, D., Nieminen, A., Agarwal, R., and Mukhtar H. (1997) Green tea constituent epigallocatechin-3-gallate and induction of apoptosis and cell cycle arrest in human carcinoma cells. J of the Nut. Cancer Inst. 89: 1881–1886.

Beg, A. A. and Baltimore, D. (1996) An essential role for NF-θB in preventing TNF-α-induced cell death. Science. 274: 782–784.

Bradford, M. M. (1976) A rapid sensitive method for the quantitation of microgram quantities of protein utilizing the principle of protein dye binding. Anal. Biochem. 200: 81–88.

Bursch, W., Oberhammer, F., and Schulte-Hermann, R. (1992) Cell death by apoptosis and its protective role against disease. TiPS. 13: 243–251.

Fang, G., Chang, B. S., Kim, C. N., Perkins, C., Thompson, C. B., and Bhalla, K. N. (1998) "Loop" domain is necessary for taxol-induced mobility shift and phosphorylation of Bcl-2 as well as for inhibiting taxol-induced cytosolic accumulation of cytochrome c and apoptosis. Cancer Research. 58: 3202–3208.

Kan W. S. (1986) Pharmaceutical Botany, 7th edition. National Research Institute of Chinese Medicine, Taiwan, ROC.

Laemmli, U. K. (1970) Nature 227: 680–685.

Li, H. -L., Liu, T. -S., Huang, T. -C., Koyama, T., and DeVol, C. -E. (1978) Flora of Taiwan, vol. 5, pp. 874–875, Epoch Publishing Co. Ltd., Taipei, ROC.

Liu, Z-G., Hsu, H., Goeddel, D. -V., and Karin, M. (1996) Dissection of TNF receptor 1 effector functions: INK activation is not linked to apoptosis while NF-κB activation prevents cell death. Cell. 87: 565–576.

Lin, J. -K., Liang, Y. -C. and Lin-Shiau. S. -Y. (1999) Cancer chemoprevention by tea polyphenols through mitotic signal transduction blockade. *Biochem. Pharm.* 58: 911–915.

Liu, X., Naekyung, C., Yang, J., Jemmerson, R., and Wang, X. (1996) Induction of apoptotic connect to text on next page program in cell-free extracts: requirement for dATP and cytochrome c. Cell Press. 86: 147–157.

Monks, A., Scudiero, D., Skehan, P., Shoemaker, R., Paull, K., Vistica, D., Hose, C., Langley, J., Cronise, P., Vaigro-Wolff, A., Gray-Goodrich, M., Campbell, H., Mayo, J., and Boyd, M. (1991) Feasibility of high-flux anticancer drug screen using a diverse panel of cultured human tumor cell lines. J. Natl. Cancer Inst. 83: 757–766.

Mosmann, T. (1983) Rapid colorimetric assay for cellular growth and survival: application to proliferation and cytotoxicity assays. J. Immunological Methods. 65:55–63.

Naujokat, C., Sezer, O., and Possinger, K. (1999) Tumor necrosis factor-α and interferon-γ induce expression of functional Fas ligand on HT29 and MCF7 adenocarcinoma cells. 264: 813–819.

Raff, M. C. (1992) Social controls on cell survival and cell death. Nature (London). 356: 397–400.

Seufferlein, T. and Rozengurt, E. (1995) Sphingosylphosphorylchokine activation of mitogen-activated protein kinase in swiss 3T3 cells requires protein kinase C and a pertussis toxin-sensitive G protein. J. Biol. Chem. 270: 24334–24342.

Skehan, P., Storeng, R., Scudiero, D. A., et al. (1990) New calorimetric cytotoxicity assay for anticancer-drug screening. J. NatI Cancer Inst. 82: 1107–1112.

Williams, G. T. (1991) Programmed cell death: Apoptosis and oncogenesis. Cell. 65: 1097–1098.

Wolf, B., and Green, D. R. (1999) Suicidal tendencies: apoptotic cell death by caspase family proteinases. 274: 20049–20052.

Wright, S. S., Zhong, J., and Larrick, J. W. (1994) Inhibition of apoptosis as a mechanism of tumor promotion. FASEB J. 8: 654–660.

Yang, J., Liu, X., Bhalla, K., Naekyung, K., Ibrado, A. M., Cai, J., Peng, T. I., Jones, D. P., and Wang, X. (1997) Prevention of apoptosis by Bcl-2: release of cytochrome c from mitochondria blocked. Science. 275: 1129–1132.

Zhang, G., Gurtu, V., Kain, S. R., and Yan, G. (1997) Early Detection of Apoptosis Using a Fluorescent Conjugate of Annexin V. BioTechniques 23: 525–531.

The terms and expressions which have been employed are used as terms of description and not of limitation, and there is no intention in the use of such terms and expressions of excluding any equivalents of the features shown and described or portions thereof, it being recognized that various modifications are possible within the scope of the present invention. The references referred to herein are incorporated by reference in their entirety.

We claim:

1. A method of treating an organism having a tumor comprising administering to said organism an effective amount of a composition comprising an extract of *Anoectochilus formosanus,* wherein the extract is obtained by a process comprising: extracting plant tissue of *Anoectochilus formosanus* with a hot water at 90 to 100° C. to form a crude extract; and further subjecting the crude extract to stepwise gradient fractionation with an organic solvent to form one or more fractions.

2. The method of claim 1 wherein the organic solvent is ethanol.

3. The method of claim 2 wherein the fraction is 87.5% ethanol soluble and the fraction comprises adenosine and isorhamnetin 3-O-β-D-glucopyranoside.

4. The method of claim 3 wherein the fraction is further extracted with ethyl acetate to produce a subfraction and said administered composition comprises said subfraction.

5. The method of claim 4 wherein the subfraction comprises α-amyrin trans-p-hydroxy cinamate and isorhamnetin.

6. The method of claim 1 wherein the composition is administered to the organism by one of intra-tumoral, intra-peritoneal or oral administration.

7. The method of claim 1 wherein the plant tissue of *Anoectochilus formosanus* is homogenized before extracting with the hot water.

8. The method of claim 1 wherein the plant tissue of *Anoectochilus formosanus* is extracted with the hot water for 0.1 to 500 minutes.

* * * * *